US010486199B2

(12) United States Patent
Justice et al.

(10) Patent No.: US 10,486,199 B2
(45) Date of Patent: Nov. 26, 2019

(54) METHOD AND APPARATUS FOR SORTING HAVING A BACKGROUND ELEMENT WITH A MULTIPLICITY OF SELECTIVE ENERGIZABLE ELECTROMAGNETIC EMITTERS

(71) Applicants: Timothy L. Justice, Walla Walla, WA (US); Johan Calcoen, Leuven (BE); Gerald R. Richert, Walla Walla, WA (US); Bert Dirix, Linter (BE)

(72) Inventors: Timothy L. Justice, Walla Walla, WA (US); Johan Calcoen, Leuven (BE); Gerald R. Richert, Walla Walla, WA (US); Bert Dirix, Linter (BE)

(73) Assignee: Key Technology, Inc., Walla Walla, WA (US)

(*) Notice: Subject to any disclaimer, the term of this patent is extended or adjusted under 35 U.S.C. 154(b) by 136 days.

(21) Appl. No.: 15/868,027

(22) Filed: Jan. 11, 2018

(65) Prior Publication Data

US 2019/0210068 A1 Jul. 11, 2019

(51) Int. Cl.
*B07C 5/342* (2006.01)
*G01N 21/84* (2006.01)

(52) U.S. Cl.
CPC ............ *B07C 5/342* (2013.01); *B07C 5/3422* (2013.01); *G01N 21/84* (2013.01); *B07C 2501/0018* (2013.01); *G01N 2201/06113* (2013.01); *G01N 2201/10* (2013.01)

(58) Field of Classification Search
CPC ..... B07C 5/342; G01N 21/84; G01N 21/8806

USPC .............................................. 250/221, 223 R
See application file for complete search history.

(56) References Cited

U.S. PATENT DOCUMENTS

| 6,914,678 | B1* | 7/2005 | Ulrichsen | ............... B07C 5/342 356/429 |
|---|---|---|---|---|
| 9,266,148 | B2 | 2/2016 | Adams et al. | |
| 9,517,491 | B2 | 12/2016 | Adams et al. | |
| 9,573,168 | B2 | 2/2017 | Adams et al. | |
| 9,795,996 | B2 | 10/2017 | Adams et al. | |

OTHER PUBLICATIONS

Notification of Transmittal of the International Search Report and the Written Opinion of the International Searching Authority, or the Declaration, PCT/US2018/61512, Mar. 15, 2019.

* cited by examiner

Primary Examiner — Que Tan Le
(74) Attorney, Agent, or Firm — Randall Danskin P.S.

(57) ABSTRACT

A method and apparatus for sorting is described, and which includes an arrangement for controllably and operably coupling to a controller, and then selectively energizing each of a background element; laser scanner; first and second electromagnetic radiation detectors; line scan imaging assembly; and selectively energizable radiators, so as to improve the detection of individual products and/or other objects of interest forming a product stream by increasing the contrast of the respective products or specific characteristics thereof, and/or objects of interest in a multiplicity of electrical signals which are received, and then processed by the controller, as the product stream passes through an inspection station.

49 Claims, 13 Drawing Sheets

METHOD AND APPARATUS FOR SORTING HAVING A BACKGROUND ELEMENT WITH A MULTIPLICITY OF SELECTIVE ENERGIZABLE ELECTROMAGNETIC EMITTERS

TECHNICAL FIELD

The present invention relates to a method and apparatus for sorting which generates multi-modal, multi-spectral images containing multiple channels of data, and which further contains information on color; polarization; fluorescence; texture; translucence; and other information which comprises many aspects or characteristics of a generated feature space, and which further can be used to represent images of objects for identification and feature and flaw detection.

BACKGROUND OF THE INVENTION

In our U.S. Pat. No. 9,517,491 and which was issued on Dec. 13, 2016, we disclosed a method and apparatus for sorting which has been employed with a great deal of commercial success to address previous problems associated with identifying products within a product stream using multiple optical, and other sensors in a manner which avoids several previously known technical problems. In particular, we described in this patent, previous attempts which have been made to enhance the ability to image objects effectively, in real-time, in view of the known problems associated with the actuation of sensors, and other cameras, in real-time. In the above-identified, and other US patents, we have defined "real-time" as meaning the electrical signal processing which occurs within the span of, and substantially at the same rate as that which is depicted. In the present patent application "real time" may include several micro seconds to a few milliseconds. One of the chief difficulties associated with such efforts to image or view a stream of objects during these time intervals has been that when particular detectors, sensors, and the like, have been previously employed, and then energized, both individually, and in combination with each other, they often have had undesirable effects, and limitations, including, but not limited to, a lack of isolation of the signals of different modes, but which have similar optical spectrums; unwanted changes in the response per optical angle of incidence, and field angle; and/or a severe loss of sensitivity or effective dynamic range of the sensor being employed, among many other issues. Thus the use of many sensors or interrogating means for providing information regarding the objects being sorted, when actuated simultaneously, often destructively interfere with each other thus limiting the ability to identify features or characteristics of an object which would be helpful in classifying it as being either, on the one hand, an acceptable product or object of interest, or on the other hand, an unacceptable one, and which needs to be excluded from the product stream, or perhaps diverted into a different processing stream where it can then be treated, and then later sold, for example, as a different grade of the same product.

While the teachings of this, and other U.S. patents have been quite successful in addressing the myriad of issues surrounding this destructive interference which can arise, and then limit the usefulness of using multiple sensors, cameras, and the like, in sorting devices of assorted designs, developers of this same technology have endeavored to develop an effective means whereby such an apparatus may be optimized to improve an optical contrast generated between the respective objects of interest or products to be inspected, and the surrounding inspection station through which these objects and/or products pass, thereby optimizing the ability for such an apparatus and related methodology to identify both acceptable and unacceptable objects of interest and/or products, and thereby perform more effective sorting of a product stream thus achieving greater benefits for an end user or customer.

A method and apparatus for sorting which avoids the detriments associated with the various prior art teachings and practices utilized, heretofore, is the subject matter of the present application.

SUMMARY OF THE INVENTION

A first aspect of the present invention relates to a method of sorting which includes moving a product stream formed of individual objects of interest to be sorted through an inspection station; selectively energizing a background element which is located adjacent to the inspection station so as to generate one or more discrete, first electromagnetic radiation bands, and directing the discrete, first electromagnetic radiation bands towards the moving product stream passing through the inspection station; energizing, in a selective manner, one or more radiators which are located adjacent to the inspection station so as to individually generate one or more discrete, second electromagnetic radiation bands, and directing the one or more second, discrete, electromagnetic radiation bands towards the moving product stream passing through the inspection station; positioning adjacent to the inspection station individual electromagnetic radiation detectors for detecting the first and second, discrete, electromagnetic radiation bands which are emitted, and either reflected or transmitted by the objects of interest to be sorted; or generated by the background element when the background element is energized, or is reflected from the background element when the background element is either energized or deenergized; and controllably coupling a controller to one or more of the selectively energizable radiators; the selectively energizable background element; and the respective, electromagnetic radiation detectors, and selectively optimizing the energizing and operation of the one or more radiators, the background element, and the electromagnetic radiation detectors, in real-time, and by way of the controller, while detecting the objects of interest and/or products with the respective electromagnetic radiation radiators and detectors, and simultaneously, either encouraging and/or inhibiting the detection of the respective objects of interest and/or products by at least some of the electromagnetic radiation detectors so as to improve a contrast generated or created between the respective objects of interest and/or products, and the energized and deenergized background element, during the detection of the objects of interest and/or products which are passing through the inspection station.

Another aspect of the present invention relates to a method of sorting which includes providing an inspection station having spaced, opposite sides, and a line of sight which is defined between, and is parallel to, the opposite, first and second sides; providing a background element, and positioning the background element on the first side of the inspection station, and wherein the background element has a multiplicity of selectively energizable electromagnetic radiation emitters which emit a first band of electromagnetic radiation when energized, and which further has an optically transmissive, electromagnetic radiation diffuser element which encloses, at least in part, the multiplicity of selectively energizable electromagnetic radiation emitters; supplying a stream of products to be sorted, and releasing the stream of products, under the influence of gravity, for movement through the inspection station, and through, and along the line of sight; positioning a laser scanner on the second side of the inspection station, and selectively energizing the laser scanner so as to emit a laser flying spot beam formed of a second band of electromagnetic radiation having predetermined wavelengths, and wherein the laser flying spot beam is repeatedly directed along the line of sight, and toward the background element which is positioned on the first side of the inspection station; providing a first electromagnetic radiation detector which is located on the second side of the inspection station, and operationally coupling the first electromagnetic radiation detector with the laser scanner; providing a second electromagnetic radiation detector which is located on the second side of the inspection station, and operationally coupling the second electromagnetic radiation detector with the laser scanner; providing a line scan imaging assembly, and positioning the line scan imaging assembly on the second side of the inspection station, and further orienting the line scan imaging assembly in optical receiving relation relative to the line of sight and the background element; providing a radiator, and selectively energizing the radiator so as to emit a third band of electromagnetic radiation having predetermined wavelengths, and which illuminates the line of sight, and the stream of products passing through the inspection station; and controllably and operably coupling a controller to each of the background element; laser scanner; first and second electromagnetic radiation detectors; line scan imaging assembly; and the selectively energizeable radiator, and which further selectively energizes the respective background element; laser scanner; illuminator; and/or line scan imaging assembly so as to improve the detection of the individual products, and other objects of interest in the product stream, by increasing the contrast of the respective products, and/or objects of interest in a multiplicity of electrical image signals which are generated, and then received by the controller, as the product stream, having the products, or objects of interest, pass through the inspection station.

Another aspect of the present invention relates to an apparatus for sorting which includes an inspection station having spaced, opposite, first and second sides, and a line of sight is defined and established between, and is parallel to the opposite, first and second sides; a background element positioned on the first side of the inspection station, and having a multiplicity of selectively energizable electromagnetic radiation emitters, and an optically transmissive, electromagnetic radiation diffuser element which encloses, at least in part, the multiplicity of selectively energizable electromagnetic radiation emitters, and which further, when energized, emits predetermined, first, electromagnetic radiation bands; a stream of products to be sorted, and which are released, under the influence of gravity, for movement through the inspection station, and through the line of sight; a laser scanner positioned on the second side of the inspection station, and which, when energized, emits a laser flying spot beam formed of a second band of electromagnetic radiation having predetermined wavelengths, and wherein the laser flying spot beam is repeatedly directed along the line of sight, and toward the background element which is positioned on the first side of the inspection station; a first electromagnetic radiation detector which is located on the second side of the inspection station, and which is further operationally coupled with the laser scanner; a second electromagnetic radiation detector which is located on the second side of the inspection station, and which is further operationally coupled with the laser scanner; a line scan imaging assembly positioned on the second side of the inspection station, and which is further oriented in optical receiving relation relative to the line of sight and the background element; a selectively energizable radiator which, when energized, emits a third band of electromagnetic radiation having predetermined wavelengths, and which illuminates the line of sight, and the stream of products passing through the inspection station, and along the line of sight; and a controller operably, and controllably coupled to each of the background element; laser scanner; first and second electromagnetic radiation detectors; line scan imaging assembly; and selectively energizeable radiator, and which selectively energizes the respective background element; laser scanner; radiator; and/or line scan imaging assembly so as to improve the detection of the individual products, and/or other objects of interest in the product stream, by increasing the contrast of the respective products, and objects of interest in a processed electrical image signal generated by the first and second electromagnetic radiation detectors, and line scan imaging assembly, as the product stream having the products, and/or objects of interest pass through the inspection station.

Still yet another aspect of the present invention relates to an apparatus for sorting which includes an inspection station having spaced, opposite, first and second sides, and which further defines an intermediate region located between the opposite, spaced, first and second sides, and wherein a line of sight is defined within the intermediate region, and is in substantially parallel relation relative to the opposite, first and second sides; a background element positioned on the first side of the inspection station, and which comprises a multiplicity of selectively energizable electromagnetic emitters, and which, when energized, individually emits a first band of electromagnetic radiation having discreet wavelengths, and which further is emitted in the direction of the line of sight, and towards the second side of the inspection station; and an optically transmissive, electromagnetic radiation diffuser element which is made integral with the background element, and which further encloses, at least in part, the multiplicity of selectively energizable electromagnetic radiation emitters, and diffuses the first band of electromagnetic radiation which is generated by the enclosed, electromagnetic radiation emitters; a stream of products to be sorted, and which are released, under the influence of gravity, for movement through the inspection station, and along the line of sight, and wherein the stream of products include at least some products and/or objects of interest having either acceptable, or unacceptable product or object features, as well as other objects of interest; a laser scanner, which when energized, emits a laser flying spot beam formed of a second band of electromagnetic radiation having predetermined wavelengths, and which is further positioned on the second side of the inspection station, and wherein the laser flying spot beam is repeatedly directed along the line of sight, and toward the background element which is positioned on the first side of the inspection station, and wherein the second band of electromagnetic radiation forming the laser flying spot beam is reflected from any one of the products in the product stream passing through the inspection station; the background element; an object of interest present in the product stream; and/or all of the foregoing; a first electromagnetic radiation detector which is located on the second side of the inspection station, and which is further operationally coupled with the laser scanner, and wherein the first electromagnetic radiation detector is rendered operable to detect only the wavelengths of the first band of electromagnetic radiation which is emitted by the background element, and diffused by the diffuser element, and generates a corresponding electrical signal; a second electromagnetic radiation detector which is located on the second side of the inspection station, and which is further operationally coupled with the laser scanner, and wherein the second electromagnetic radiation detector is rendered operable to detect only the wavelengths of the second band of electromagnetic radiation which are emitted by the laser scanner, and which are further reflected from the background element and/or any one of the products or objects of interest traveling in the product stream, and which are further passing through the inspection station, and along the line of sight, and which further generates a corresponding electrical signal; a line scan imaging assembly positioned on the second side of the inspection station, and which is further oriented in optical receiving relation relative to the line of sight and the background element, and wherein the line scan imaging assembly receives, and detects the first band of electromagnetic radiation which is emitted by the background element, and which is then diffused by the diffuser element, and wherein the line scan imaging assembly forms an electrical image signal which represents an image of the product stream passing through the inspection station, and along the line of sight; a selectively energizable radiator which, when energized, emits a third band of electromagnetic radiation having predetermined wavelengths which illuminate the line of sight, and the stream of products which may include other objects of interest passing through the inspection station, and along the line of sight; and a controller operably, and controllably coupled to each of the background element; laser scanner; first and second electromagnetic radiation detectors; line scan imaging assembly; and selectively energizeable radiator, and which further receives, and processes the electrical signals generated by each of the first and second electromagnetic radiation detectors, and the electrical image signal generated by the line scan imaging assembly, and wherein the controller selectively energizes the respective background element; laser scanner; radiator; and/or line scan imaging assembly so as to improve the detection of the individual products, and other objects of interest in the product stream, by increasing the contrast of the respective products, and the objects of interest in the electrical image signals processed by the controller as the product stream having the products, or objects of interest pass through the inspection station.

These and other aspects of the method and apparatus for sorting of the present invention will be discussed in greater detail, hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
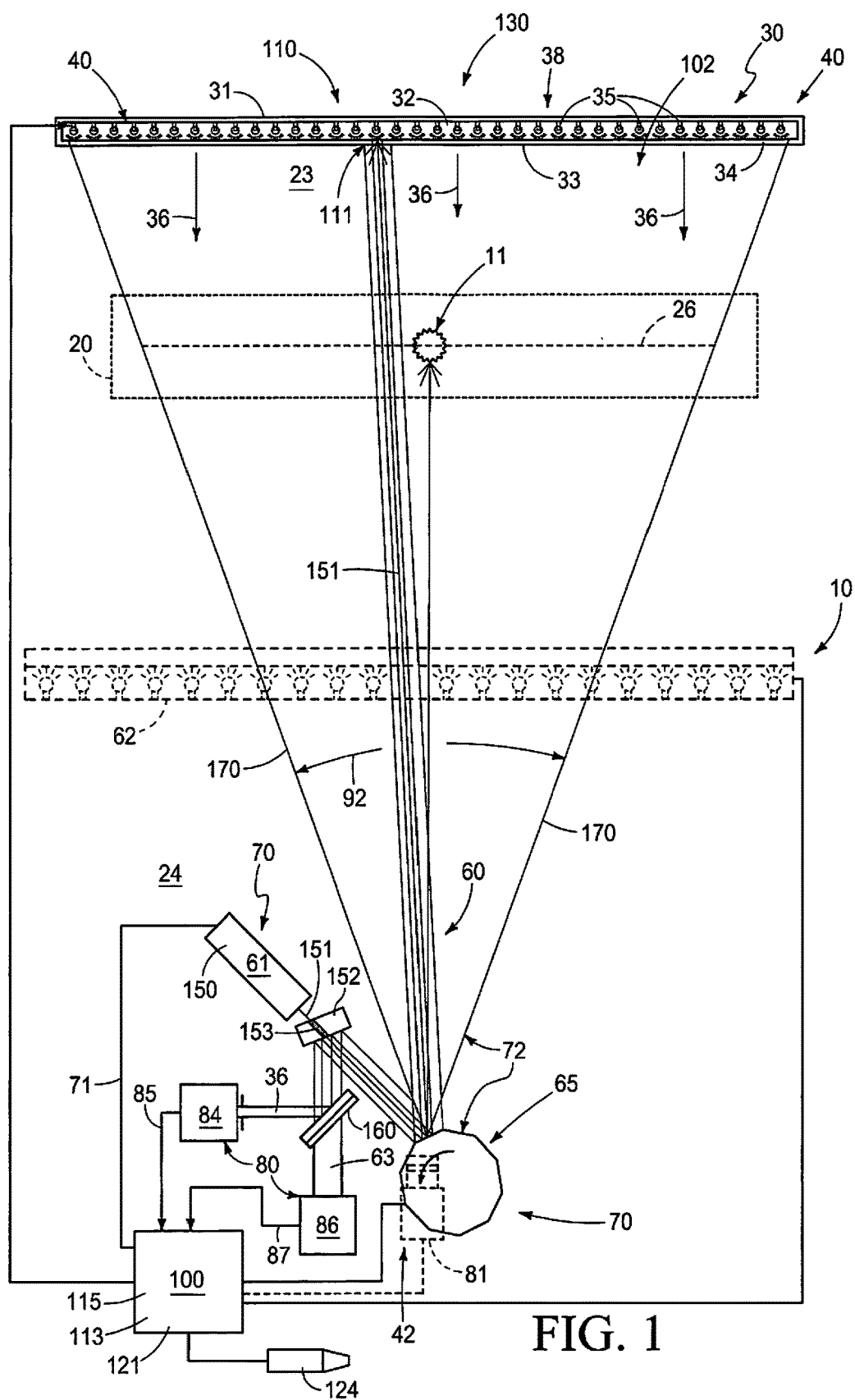
FIG. 1 is a greatly simplified, plan, schematic view of one form of an apparatus which is arranged so as to implement the methodology of the present invention.

This disclosure of the invention is submitted in furtherance of the constitutional purposes of the U.S. Patent Laws "to promote the progress of science and useful arts" (Article 1, Section 8).

The present invention 10 as described, hereinafter, provides an effective means for improving the contrast generated between the respective objects of interest, or products to be sorted, and the inspection station through which the objects of interest or products are passing in a manner which has not been possible, heretofore. As earlier discussed in U.S. Pat. No. 9,517,491, and other patents which claim priority from this same U.S. patent, the disclosed inventions provide a convenient means whereby the effects of destructive interference, which might occur upon the substantially simultaneous energizing of various sensors utilized to detect the presence of objects of interest or products traveling in a product stream, may be effectively avoided. In particular, the aforementioned U.S. patents, describe, in detail, a temporal (time) synchronization methodology, in combination with phase controlled, detector or interrogation isolation methodology which avoids the aforementioned destructive interference problems. This methodology, as described in this, and other patents was done in selective and variable combinations. While the inventions as described in this and other U.S. patents support, and allow for the use of more common devices such as, optical beam splitters; spectral or dichroic filters; and polarization elements of various designs to isolate, and combine the optical outputs of different detectors or interrogators, the inventions, as previously described, in this and other U.S. patents, provide an effective means for separating, and/or selectively and constructively combining image or signal data from detection or interrogation sources that would otherwise destructively interfere with each other. As noted in these earlier patents, while the prior art methods in existence employ beam splitters, dichroic spectral filters, and/or polarizing elements in various ways or combinations, these devices, and the associated methodology associated with their utilization, both individually, and in combination with each other, have many undesirable effects, and limitations including, but not limited to, a lack of isolation of signals of different modes, but similar optical spectrums; unwanted changes in a response per optical angle of incidence, and field angles; and/or a severe loss of sensitivity or affected dynamic range. The teachings of U.S. Pat. No. 9,517,491 are incorporated by reference herein.

Notwithstanding the teachings, noted above, and the success that has been achieved with the use of the aforementioned invention as described in this, and other U.S. patents, several of the earlier inventors detected, while developing, and then recently deploying new commercial products which incorporate the previous inventions, that on observed occasions where destructive interference occurred during the operation of the various sensors, and other interrogation devices employed with same, that the inventors were able to discern or detect, at least in some acquired image data, improved contrast which was generated between respective objects of interest or products being sorted, and an energized and deenergized background element during the detection of the objects of interest or products while they were passing through an inspection station. This discovery flew against the common wisdom as expressed in the prior art. After receiving this surprising result, the inventors began a series of experiments to determine the causation of the discerned and improved contrast. Continued research, and experimentation, resulted in the development of the present method and apparatus 10 of the invention which employs methodology which is contra-indicated by the conventional wisdom, and expressed teachings of the prior art, but yet achieves or otherwise facilitates the improved identification of acceptable and unacceptable products and/or other objects of interest traveling in a product stream, and which is subsequently sorted.

Conventional wisdom follows that, for a flying spot light (i.e. electromagnetic radiation) beam type imaging scanner, spatial resolution is governed by the size of the generated spot, for example, 0.5 mm. For example, a smaller spot of light supports greater spatial resolution, as in the ability to resolve smaller objects of interest and the features of same, to greater detail, within a resulting image of the objects, and features. The prior art teachings further shows that the size of operably coupled electromagnetic radiation detector apertures directly affects the detector's reflection scatter response. A relatively large aperture, (for example 4-9 mm in diameter), delivers a broad range of reflected light scatter to a detector. A smaller aperture, (for example 1-1.5 mm in diameter), selects light reflections that are less scattered, and more local to the reflection and scattering effect of the flying spot light beam when it optically interacts with an object or surface of the object. A centrally oriented obscuration which is formed or otherwise oriented within a larger aperture, (for example a 1.5-2.5 mm diameter obscuration which is positioned within a 5-9 mm diameter aperture), selects light reflections that are more scattered about the periphery of the flying spot light beam upon an object or surface. Furthermore, conventional wisdom supports the use of larger apertures through which to collect more reflected electromagnetic scatter from the reflection and scattering effect of the flying spot light beam upon an object or surface, as the electromagnetic radiation from such reflected scatter is commonly only a small fraction of that of the flying spot light beam electromagnetic radiation source. Therefore, as supported by convention, and earlier prior art teachings, a relatively larger electromagnetic radiation detector aperture can be used to collect more electromagnetic radiation from reflected scatter even though a larger aperture generally reduces the resulting spatial resolution because, for a flying spot light beam scanner, spatial resolution is governed significantly by the size of the spot of light. In summary, therefore, conventional wisdom teaches the generation of small spots of light, and employing electromagnetic radiation detectors with relatively large apertures so as to optimize the sensitivity of the electromagnetic radiation detectors to small amounts of reflected electromagnetic scatter, while simultaneously maintaining sub-millimeter spatial resolution.

The present invention 10, on the other hand, is constructed and operated contrary to the aforementioned convention, and teachings by employing a much smaller electromagnetic radiation detector aperture which is an order of magnitude smaller than even the smallest apertures commonly used heretofore, (for example 100-150 microns in diameter), and further, by generating electromagnetic radiation from a large fixed light source with a lower spot intensity, (for example >1 m in length). It is also possible to effectively form the above-mentioned, much smaller aperture, by the use of a small scale telescopic lens (not shown) to gather light into the electromagnetic radiation detector, and also constrain the area of focus of the electromagnetic radiation detector's view to that which is similar to an aperture which is, for example 100-150 microns in diameter. From a conventional approach, such a small aperture would not normally collect enough light, particularly when used with a light source producing less spot intensity. Convention further suggests that a large light source does not provide sufficient spatial resolution. The current invention avoids these shortcomings by scanning a large fixed light source directly with a flying spot beam not formed of light but of the effective, non-visible projection of a small area of focus allowed by the much smaller detector aperture, from the opposite side of objects of interest such that the objects of interest at least partially occlude the electromagnetic detector's view of the large fixed light source over the small area of focus allowed by the much smaller electromagnetic radiation detector aperture. This view alone provides an indication of presence, size, shape and position of objects of interest 11, but does not also provide a good indication of reflected electromagnetic radiation scattered by the near surface of the object of interest 11. To avoid this shortcoming the current invention 10 further includes a second electromagnetic radiation detector 86, of more conventional design, and that is optically co-aligned with the first electromagnetic detector 84 which includes the much smaller aperture. The second electromagnetic radiation detector 86 is further coupled with an individual electromagnetic radiator 70 (and which also includes radiation 61), and which is aligned to produce a small flying spot light beam 71 that effectively scans the near surface of objects of interest 11 which then reflect the electromagnetic radiation scattered back to the second detector 86, thus providing a good indication of reflected electromagnetic radiation scattered by the near surface of the object of interest 11 commensurate with the indication of presence, size, shape and position of objects of interest 11 provided by the first electromagnetic radiation detector 84, and which employs the much smaller aperture. While these two views provide both an indication of the presence, size, shape, and position of the objects of interest 11, and a good indication of the reflected electromagnetic radiation scattered by the near surface of the object of interest 11, the second electromagnetic radiation detector 86 is not provided with a reflection of the electromagnetic radiation scatter when, and where, no objects of interest 11 are present. To avoid this shortcoming the present invention 10 also includes a transmissive diffuser element 34 that additionally operates as a reflective diffuser to scatter light that strikes the transmissive surface, and also scatters light that passes through the transmissive surface of same. In this way both first and second electromagnetic radiation detectors 84 and 86 are provided with background based electromagnetic radiation scatter when, and where, no objects of interest 11 are present. While the large, fixed light source 62, the one or more electromagnetic radiators aligned to produce a small flying spot light beam 71, and the transmissive diffuser element 34 collectively provide electromagnetic radiation to both first and second electromagnetic radiation detectors, 84 and 86, these elements can also potentially spectrally interfere with each other due to their spatial alignment. Thus, the current invention 10 also includes a selection of first and second electromagnetic radiation bands 36 and 63 such that the first and second electromagnetic radiation detectors 84 and 86 may operate without critical levels of destructive interference. While the selection of the first and second electromagnetic radiation bands 36 and 63 can addresses critical levels of most potential spectral interference, some electromagnetic radiation bands may partially, and even substantially overlap, thereby allowing at least a partially destructive interference to take place. To overcome this potential shortcoming, the current invention 10 further includes selective energization of the one or more electromagnetic radiators, and associated detectors with each flying spot beam 71 scan 72. By selecting electromagnetic radiation bands and selectively operating one or more electromagnetic radiators and detectors, the resulting image contrast is increased between the objects of interest 11, and the features of same, and a background element 30 formed of the large fixed light source, and the transmissive diffuser element 34. To further increase a resulting image contrast, the current invention 10 adds a selectively operated line scan imaging assembly 81, with a selectively operated, and predetermined third band of electromagnetic radiation 64 as illumination. As with the first and second electromagnetic radiation detectors 84 and 86, and the first and second electromagnetic radiation bands 36 and 63 which are associated with the background element 30, and which further includes the large fixed light source, and the transmissive diffuser element 34, the one or more electromagnetic radiators 61 are aligned to produce a small flying spot light beam 71 that effectively scans the near surface of objects of interest 11; and the third band of electromagnetic radiation 64, and the line scan imaging assembly 81 can be selectively operated with partial spectral and temporal overlap, and both, selectively with, and without some selected interference, to more fully optimize, and increase a resulting contrast which is then created based, at least in part, upon the electromagnetic radiation reflective and/or transmissive behaviors of particular selected objects of interest 11. The several inventive features mentioned, above, will be further explained in the paragraphs which follow.

Figure 2:
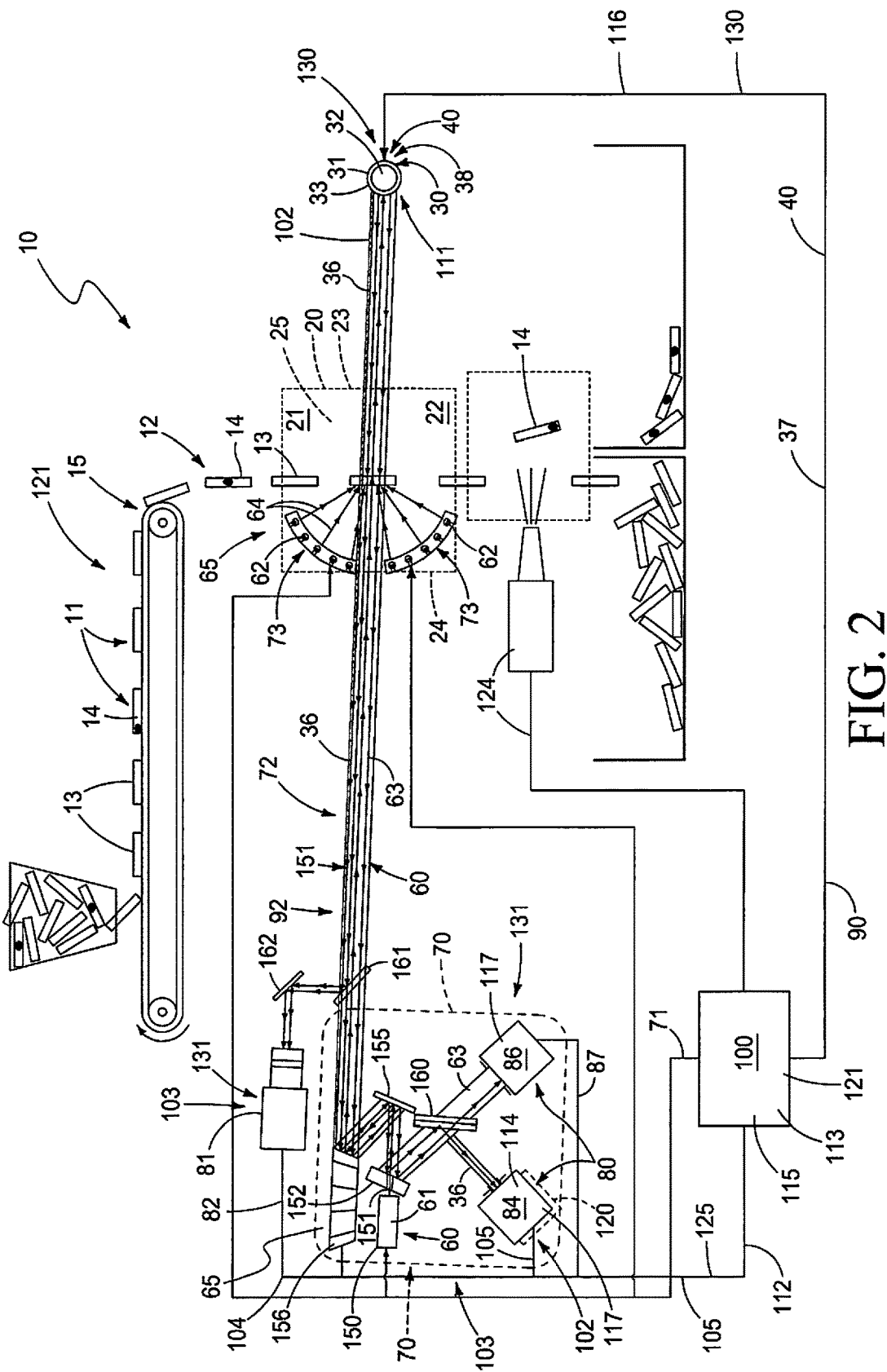
FIG. 2 is greatly simplified, side elevation, schematic view of one form of an apparatus which is arranged so as to implement the methodology of the present invention.
Figure 3:
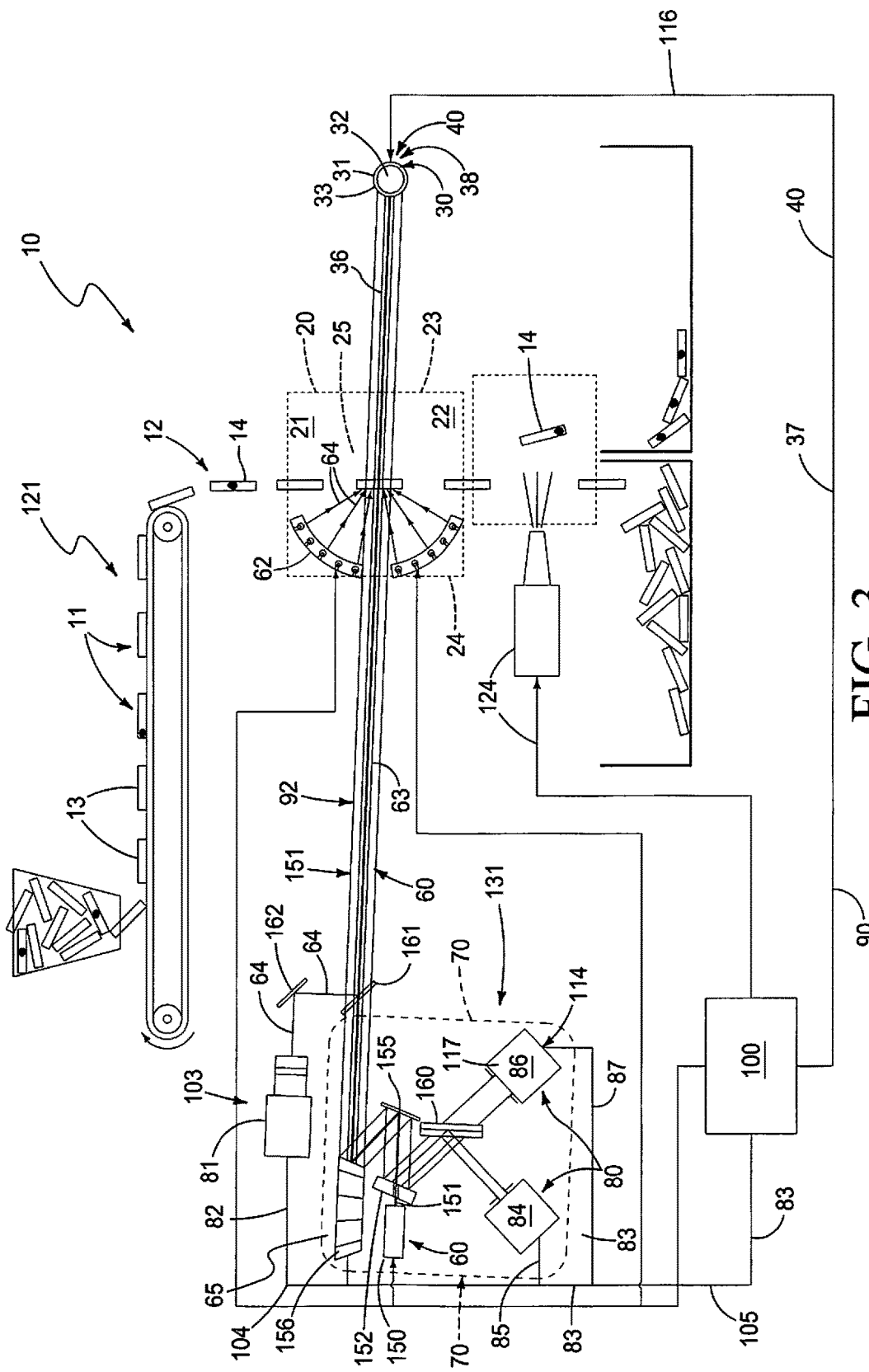
FIG. 3 is a second, greatly simplified, schematic view of one form of an apparatus which is arranged so as to implement at least some of the steps of the methodology of the present invention.

The method and apparatus of the present invention is generally indicated by the numeral 10 in FIG. 1, and following. In this regard, the method aspect of the present invention includes a step of providing a source of individual objects of interest and/or products 11 to be sorted. The individual objects of interest and/or products to be sorted and which are provided from the source 11, are formed into a product stream 12, and which includes a mixture of both acceptable objects of interest and/or products 13, and unacceptable objects of interest and/or products 14. The method of sorting 10 of the present invention includes a step 15 of moving the product stream 12 formed of the individual objects of interest and/or products 11 to be sorted through an inspection station, and which is generally indicated by the numeral 20. This movement can be achieved in one possible form of the invention by the use of gravity as seen in the attached drawings (FIGS. 2 and 3). The inspection station 20 has a first, intake end 21, and a second, exhaust end 22. Still further, the inspection station 20 has a first side 23, and a spaced, opposite, second side 24. An intermediate region 25 is defined between the first and second ends 21 and 22, and the first and second sides 23 and 24, respectively. A line of sight 26 is defined between, and is generally parallel to, the opposite first and second sides 23 and 24, of the inspection station 20, and which receives, and allows for the passage of the product stream 12, therethrough.

The method and apparatus 10 of the present invention further includes a background element which is generally indicated by the numeral 30, and which further is positioned on the first side 23, of the inspection station 20, and which still further has a main body 31, that defines an internal cavity 32. The main body 31 of the background element has an outwardly facing, and optically transmissive surface 33; and an optically transmissive diffuser element 34 which is positioned on, or made integral with, the outwardly facing surface 33, and is operable to optically interact with, and otherwise diffuse, at least in part, visible and/or invisible electromagnetic radiation in a manner which will be discussed in greater detail, hereinafter. A multiplicity of selectively energizable electromagnetic radiation emitters 35 are provided, and which are individually positioned in predetermined, spaced relation within the internal cavity 32, of the background element 30. The multiplicity of selectively energizable electromagnetic radiation emitters 35, when energized, emit first, predetermined electromagnetic radiation bands 36, and which are first passed or transmitted by the main body 31, and are then optically diffused by the optically transmissive diffuser element 34. The method of the present invention 10 includes a step 37 of selectively energizing the background element 30, which is located adjacent to the inspection station 20, so as to generate or emit the discreet, first electromagnetic radiation bands 36; and another step 38, of directing or orienting the discreet first electromagnetic radiation bands 36 towards the moving product stream 12 which is passing or travelling through the inspection station 20.

Figure 5:
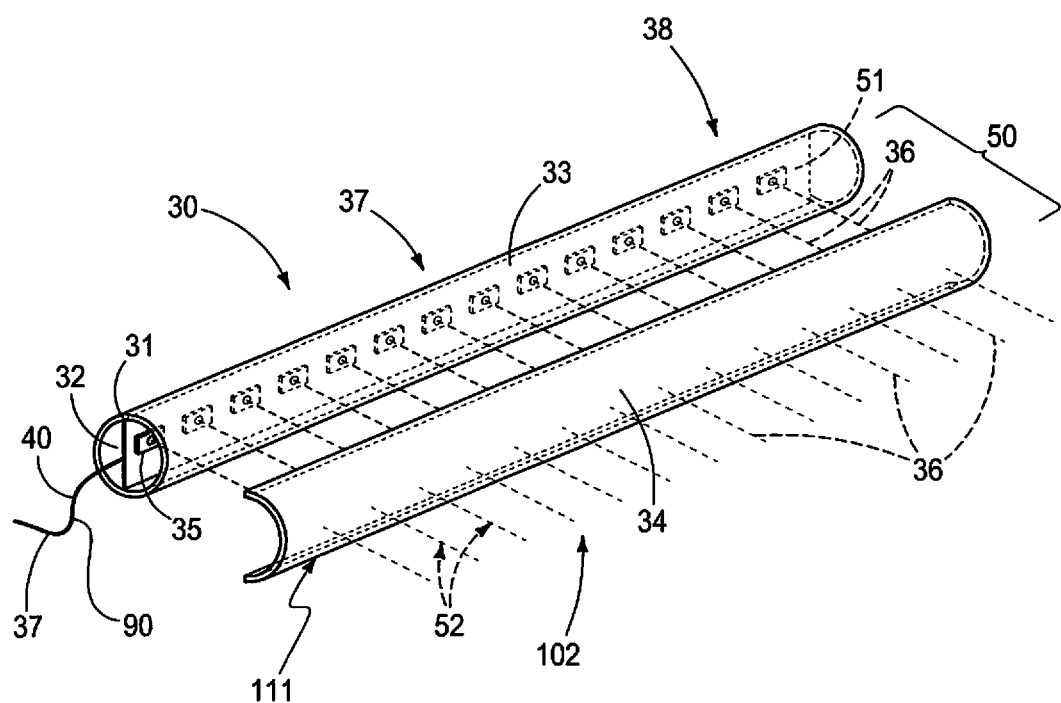
FIG. 5 is a perspective, fragmentary, side elevation view of a background element which forms a feature of the present invention.

The step 37 of selectively energizing the background element 30 further includes another step of 40 of selectively generating one or more visible or invisible electromagnetic radiation bands either simultaneously, or sequentially, by means of the background element 30. Still further, the method includes yet another step 41 of positioning the background element 30, on the first side 23, of the inspection station 20. Additionally, the methodology includes a step of directing the generated first electromagnetic radiation bands 36 towards the opposite, second side 24 of the inspection station 20. In the methodology as described, above, the step 41 of positioning the background element 30, on the first side 23 of the inspection station 20, further comprises a step 50 of first providing a background element 30, and which has both an optically transmissive electromagnetic radiation diffuser element 34, and further defines an internal cavity 32. Still further the method includes another step 51 of operably positioning a multiplicity of selectively energizable electromagnetic radiation emitters 35 within the internal cavity 32, of the background element 30 (FIG. 5). Moreover, the method 10 includes another step of operably coupling the respective electromagnetic radiation emitters 35 which are positioned within the internal cavity 32, of the background 30, with a controller, as will be described in greater detail in the paragraphs which follow. As noted, above, the method includes a step 37 of selectively energizing the respective electromagnetic radiation emitters 35 which are located within the internal cavity 32, of the background element 30, with the controller, as will be described, either simultaneously, and/or sequentially, as indicated in step 40 (FIG. 5). Still further, the method includes another step 52 of diffusing the electromagnetic radiation 36 which is emitted by the energized electromagnetic radiation emitter 35, with the optically transmissive electromagnetic radiation diffuser element 34.

The method of the present invention 10 includes another step 60 of energizing, in a selective manner, one or more radiators 61 (FIG. 2) which are located adjacent to the inspection station 20, so as to individually generate one or more discreet, second electromagnetic radiation bands 63, and directing 65 the one or more, second, discreet electromagnetic radiation bands 63 towards the moving product stream 12, and which is passing through the inspection station 20. More specifically, the step 60 of energizing, in a selective manner, the one or more radiators so as to individually generate the discreet second, electromagnetic radiation bands, further includes a step 61 of providing, and then positioning the one or more first radiators, on the second side 24, of the inspection station 20, and which further, when energized, generate 63 one or more second bands of electromagnetic radiation, having predetermined wavelengths, and which are directed or otherwise oriented along the line of sight 26. Still further, the present method 10 includes a further step of operably coupling at least one electromagnetic radiation detector, which will be discussed in the paragraphs which follow, with at least one of the first radiators 61. It should be understood that the step 61 of selecting, and then positioning the one or more first radiators on the second side 24, of the inspection station 20, further comprises a step 62 (FIG. 2) of providing one or more, second, selectively energizable radiators, and which are positioned so as to illuminate, when energized, the line of sight 26, and the stream of products 12 which are moving within the inspection station 20, with a predetermined, third band of electromagnetic radiation 64, as the product stream 12 passes along the line of sight 26. In the methodology 10 as described, above, it should be understood that in one form of the invention, the first, electromagnetic radiation bands 36 have given wavelengths which are similar to the wavelengths of the second and/or third bands of electromagnetic radiation 63 and 64, respectively. Further, and in another possible form of the invention, the first electromagnetic radiation bands 36 have given wavelengths which are dissimilar to the wavelengths of the second and/or third electromagnetic radiation bands 63 and 64, respectively.

Figure 7:
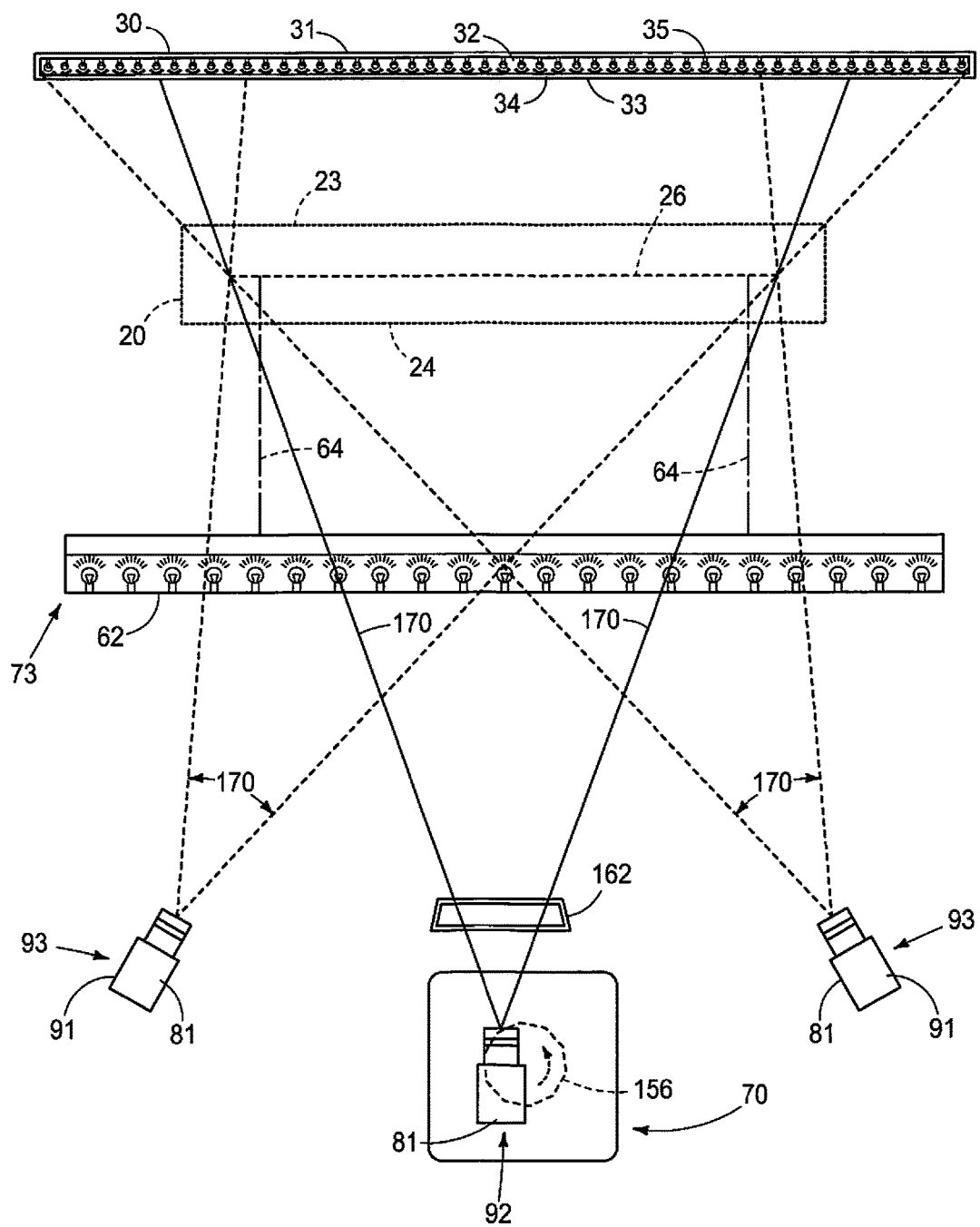
FIG. 7 is a fragmentary, greatly simplified, schematic, plan view of a portion of the present invention showing a second, possible, spatial orientation for several major components of the present invention, and which is different from that seen in FIGS. 1 and 6, respectively.

In the methodology as described, above, the step 62 of providing a selectively energizable second radiator which generates 64 a third band of electromagnetic radiation further comprises the step 73 of positioning the selectively energizable second radiator 62 which generates the third band of electromagnetic radiation 64, in a predetermined, spatial orientation relative to the inspection station 20, so as to illuminate the line of sight 26, with the third band of electromagnetic radiation 64, while simultaneously, and selectively inhibiting, an illumination of the background element 30, with the generated, third band of electromagnetic radiation 64 (FIGS. 2 and 7, respectively).

In the methodology as described above, the step 61 of selecting, and then positioning the one or more first radiators on the second side 24 of the inspection station 20 further comprises the step 70 of providing a laser scanner, and positioning the laser scanner on the second side 24, of the inspection station 20. The methodology 10 includes another step 71 of selectively energizing the laser scanner 70, with a controller, as will be described, hereinafter, so as to produce a laser flying spot beam formed of one or more visible, or invisible, second electromagnetic radiation bands 63; and another step 72, of repeatedly moving the flying spot beam along the line of sight 26, and illuminating the product stream 12 which is moving between the first and second sides 23 and 24, respectively, of the inspection station 20 (FIG. 1). The moving laser flying spot beam 71 is directed toward and optically interacts with the background element 30, and which is positioned on the first side 23 of the inspection station 20.

The laser scanner 70, as depicted in the attached drawings (FIGS. 2-4) includes a selectively energizable laser 150 which, when energized emits a discreet beam of concentrated electromagnetic radiation 151. The laser scanner further is positioned in close proximity relative to a Pritchard mirror 152, and which is placed in front, and in spaced relation relative to the of the laser 150. This type of mirror is well known, and further has a region 153 (FIG. 4) which permits the generated laser beam 151 to pass therethrough. This Pritchard mirror 152 further has a reflecting surface 154 which reflects, and then re-directs the electromagnetic radiation coming from the inspection station 20 onto the electromagnetic radiation detectors, as will be described in further detail, below. One form of the laser scanner 70 has an optional, second, reflecting mirror 155 which reflects the laser beam 151 in the direction of a rotating polygon-shaped mirror 156. This rotating, polygon-shaped mirror effects a reflection of the laser beam 151 in the direction of the inspection station 20. Further, by its shape, and continuous rotation, the polygon-shaped mirror 156 causes the laser beam 151 to repeatedly scan, in one direction, 72 along the line of sight 26 (FIG. 1), and optically interact with the background element 30, and diffuser element 34 as will be discussed, hereinafter. The laser scanner 70 further includes a first dichroic mirror 160 which is located in spaced relation relative to the laser 150, and which operates to either pass, or reflect, electromagnetic radiation which is returned from the inspection station 20, and which further may include electromagnetic radiation coming from the background element 30; and/or the objects of interest 11. The aforementioned electromagnetic radiation coming from the direction of the inspection station 20 moves in a direction towards the laser scanner 70, and then passes through a second, partial dichroic mirror 161. The second, partial, dichroic mirror 161 allows for the passing of at least a portion of the signal amplitude of selected frequencies of electromagnetic radiation, and the reflection of others. For the frequencies of electromagnetic radiation which are passed, these same frequencies of electromagnetic radiation are then reflected off of the rotating polygon-shaped mirror 156, and in at least one form of the laser scanner 70, in the direction of the second, reflecting mirror 155, and then is reflected in the direction of the reflecting surface 154, of the Pritchard mirror 152. This same electromagnetic radiation optically interacts with the dichroic mirror 160, and is then directed toward either the first or second electromagnetic radiation detectors 84 and 86, respectively. For the electromagnetic radiation which is reflected from second, partial dichroic mirror 161, this electromagnetic radiation is optionally, so as to facilitate the placement of the line can imaging assembly 81, reflected off of a third reflective mirror 162, and then in a direction toward the line scan imaging assembly 81 as seen in FIG. 2.

The method and apparatus of the present invention 10 further includes another step 80 of positioning and/or providing at a location which is adjacent to the inspection station 20, individual electromagnetic radiation detectors for detecting the first, 36, and the second, 63, discreet electromagnetic radiation bands which are emitted, and then, either reflected by the objects of interest or products 11 to be sorted; or which are further generated by the background element 30, when the background element is energized; or are reflected from the background element 30 when the background element 30 is energized or deenergized. More specifically, the step 80 of positioning adjacent to the inspection station 20 individual electromagnetic radiation detectors further comprises a step 81 of providing a line scan imaging assembly on the second side 24 of the inspection station 20, and then orienting the line scan imaging assembly relative to the line of sight 26. The method 10 includes another step of operably, and controllably coupling 82 the line scan imaging assembly 81 which has been provided, with a controller, and which further will be discussed in greater detail, hereinafter. In addition to the foregoing, the method includes a step 83 of operably coupling at least two electromagnetic radiation detectors with a controller 100. The step 83 further includes a step of providing a first electromagnetic radiation detector 84 which is positioned on the second side 24 of the inspection station 20, and which is further operably coupled with laser scanner 70; and detecting 85 with the first electromagnetic radiation detector 84 the first electromagnetic radiation bands 36 which are generated by the energized, electromagnetic radiation emitters 35, and which are enclosed within the internal cavity 32 of the background element 30. The generated first electromagnetic radiation bands are then diffused by the diffuser element 34. The method 10 includes another step 86 of providing a second electromagnetic radiation detector which is positioned on the second side 24, of the inspection station 20, and which is further operably coupled with the laser scanner 70. The method includes still another step 87 (FIG. 8) of detecting with the second electromagnetic radiation detector the second, electromagnetic radiation bands 63 which are emitted by the energized laser scanner 70, and which further are reflected, at least in part, from one of the objects of interest and/or products 11 which are traveling along in the product stream 12 or the background element 30, and passing simultaneously through the inspection station 20, and along the line of sight 26. Once the diffused and/or reflected electromagnetic radiation reaches the Pritchard mirror 152, it is then reflected to the first, dichroic mirror 160. This reflected electromagnetic radiation then, based upon its respective frequencies, either passes through, and in the direction of first, electromagnetic radiation detector 84, or alternatively, is reflected in a direction toward a second electromagnetic radiation detector 86, as described, below.

Figure 6:
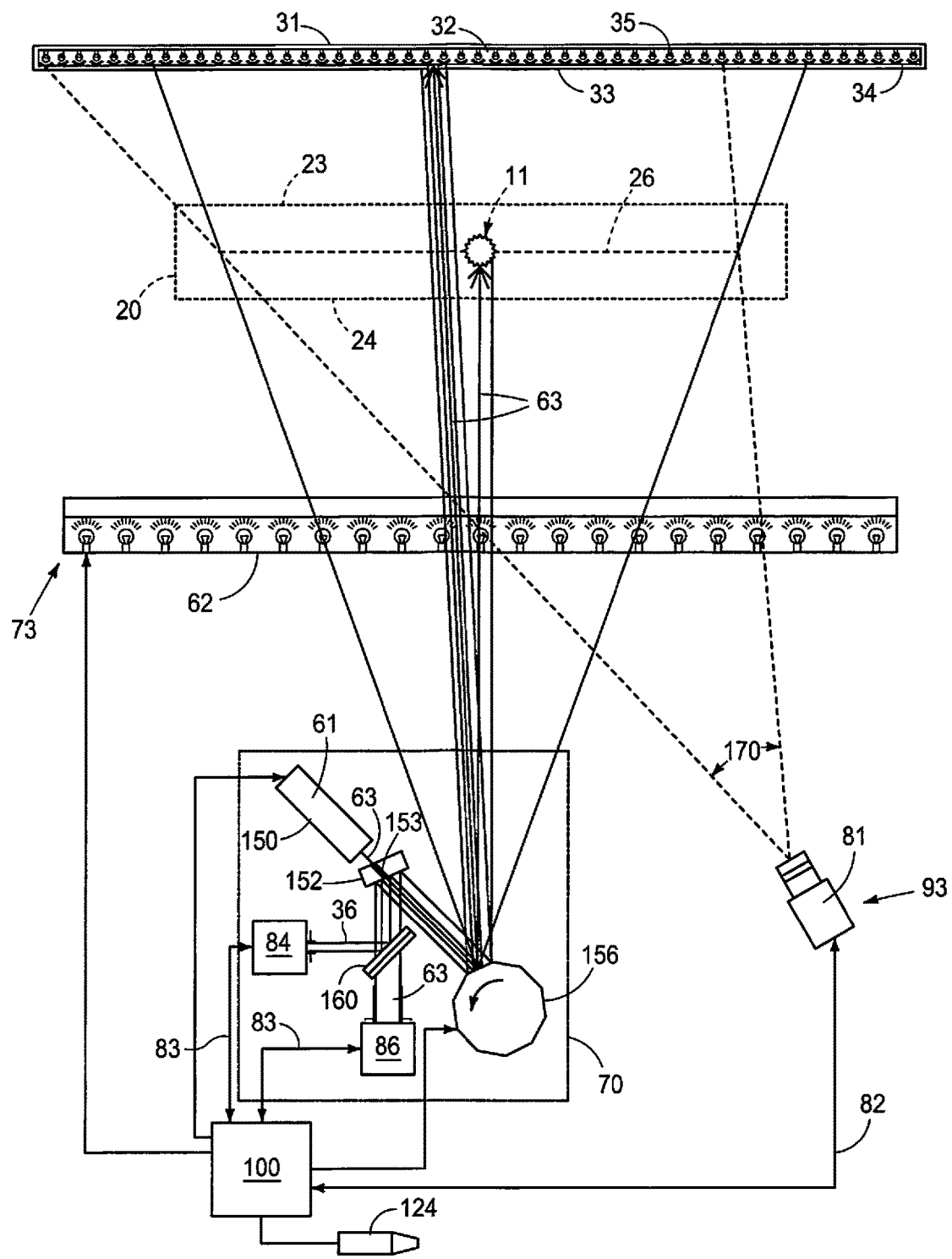
FIG. 6 is a fragmentary, greatly simplified, schematic, plan view of a portion of the present invention showing one possible spatial orientation for several major components of the present invention, and which is different from the spatial orientation as seen in FIGS. 1 and 2.

The method 10 of the present invention includes another step 90 (FIG. 5) of selectively increasing, and then decreasing the luminosity or radiance of the energized electromagnetic radiation emitters 35, and which are located within the internal cavity 32 of the background element 30, and which are further positioned on the first side 23, of the inspection station 20; and the one or more selectively energizable radiators 62 which are located on the second side of the inspection station 20. As mentioned, above, the step 81 of providing a line scan imaging assembly further comprises a step of providing multiple line scan imaging assemblies 91 (FIG. 7); and positioning 92 each of the line scan imaging assemblies so as to have a view of the same line of sight 26, and a common diffuser element 34, and which forms, at least in part, a portion of the background element 30 (FIGS. 1 and 6, respectively). In the present methodology 10, the step of providing the laser scanner 70, and the line scan imaging assembly 81 further comprises a step 93 (FIG. 7) of positioning each of the laser scanner 70, and the line scan imaging assembly 81 so as to have a dissimilar viewing orientation relative to the line of sight 26. In the methodology of the present invention 10, the step 62 of providing one or more selectively energizable, second radiators which generates 64 a third band of electromagnetic radiation, further comprises a step 65 of positioning the one or more selectively energizable, second radiators 62, and which generate 64 the third band of electromagnetic radiation, in a predetermined spatial orientation relative to the inspection station 20, so as to illuminate the line of sight 26, with the third band of electromagnetic radiation 64, and while simultaneously and selectively inhibiting an illumination of the background element 30, with the third band of electromagnetic radiation 64 (FIG. 2). Each of the line scan imaging assemblies 81, (FIGS. 1, 6 and 7) have a field of view (FOV) 170 which visually perceives the line of sight 26, and through which the product stream 12 passes.

Figure 8:
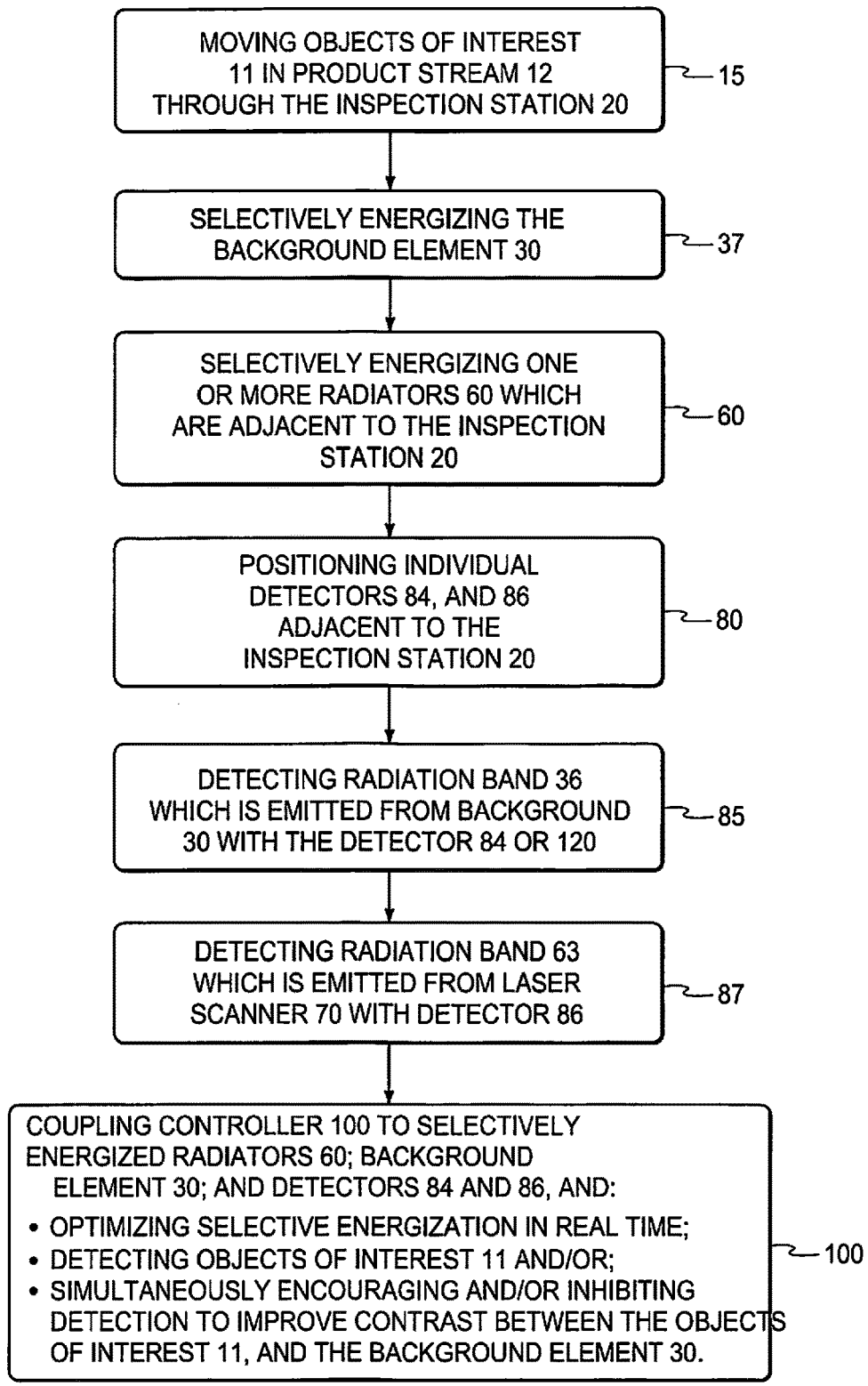
FIG. 8 is a flow diagram depicting several major steps in the methodology of the present invention.
Figure 9:
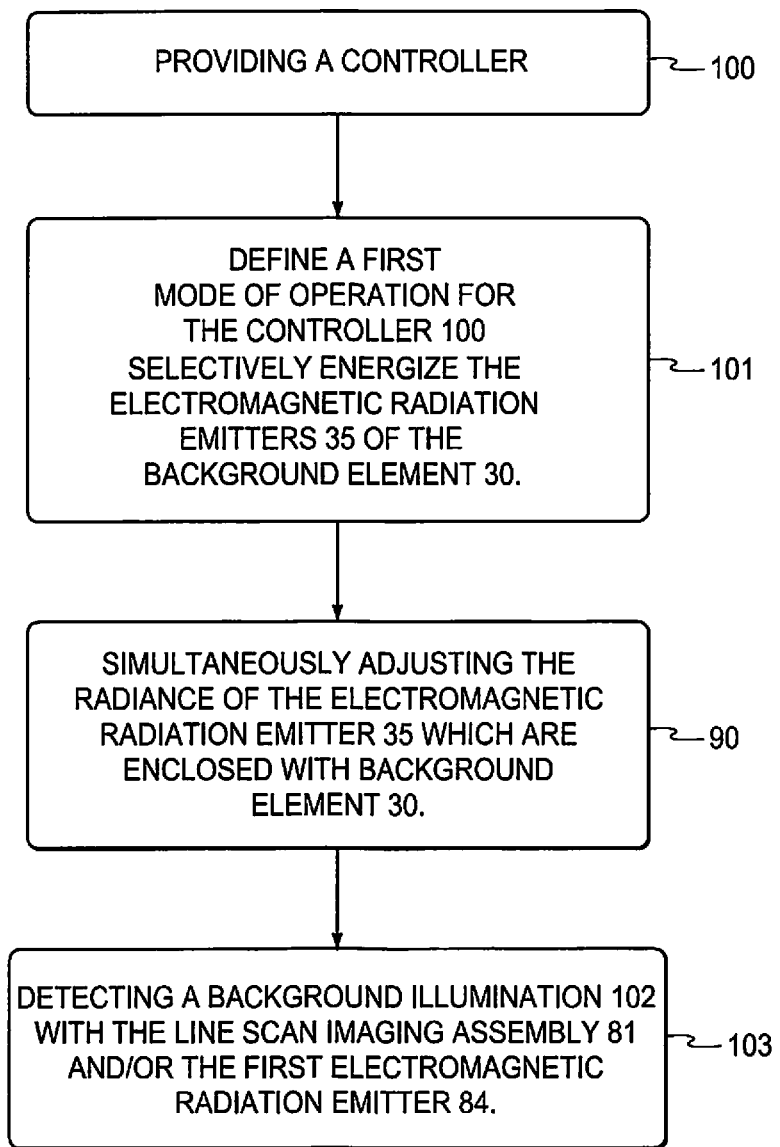
FIG. 9 is a second method step flow diagram depicting several additional steps in the methodology of the present invention.
Figure 10:
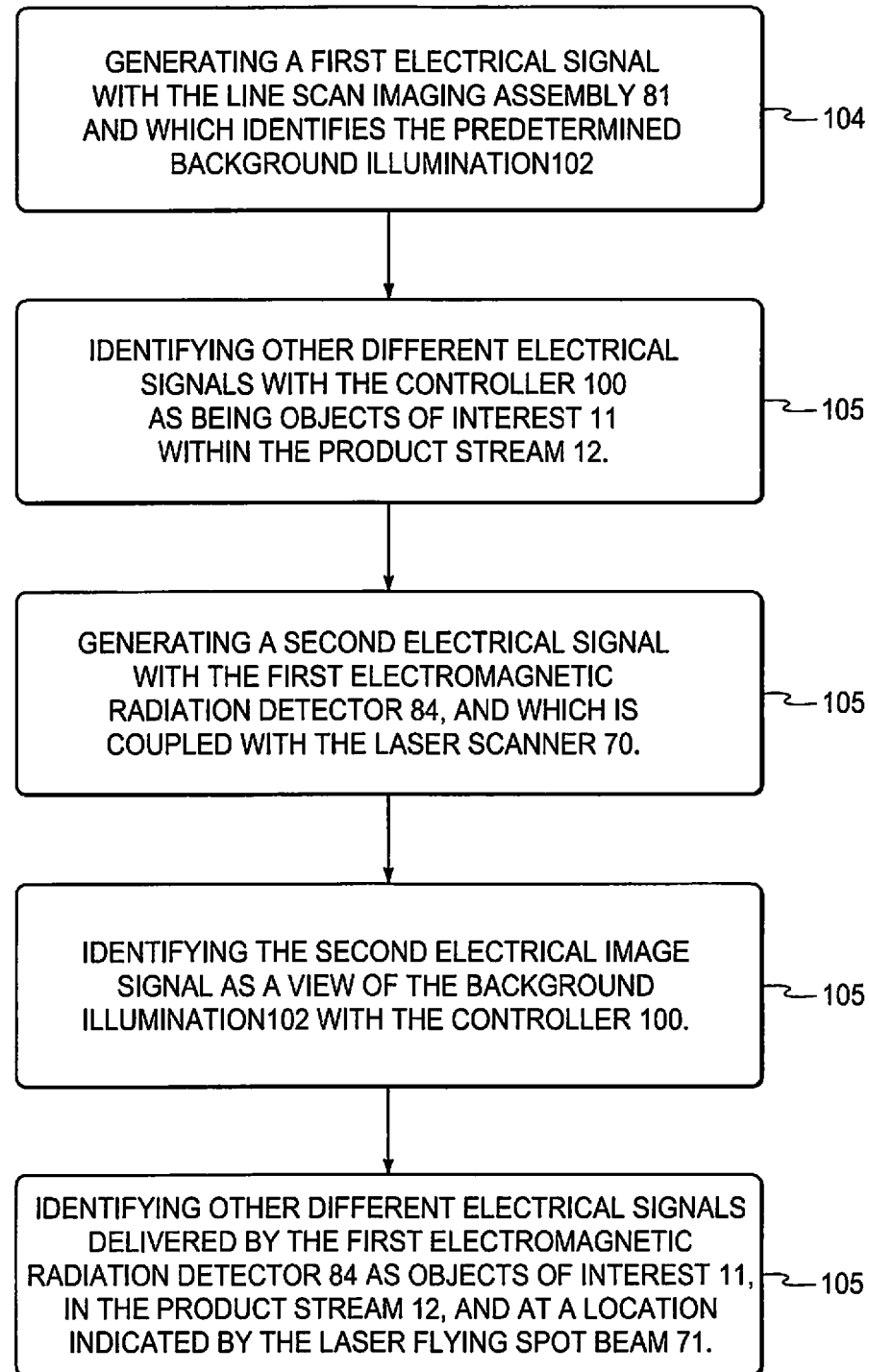
FIG. 10 is a third method step flow diagram depicting several additional steps in the methodology of the present invention.

The methodology of the present invention includes a step 100 (FIGS. 3, 8 and 9) of controllably coupling a controller to one or more of the selectively energizable radiators 60; selectively energizable background element 30; and the respective electromagnetic radiation detectors 84 and 86, respectively, and further, selectively optimizing the energizing and operation of each of the radiators 60; background element 30; and electromagnetic radiation detectors 84 and 86, respectively, in real time, and by way of the controller 100, and while simultaneously detecting the objects of interest and/or products 11, with the respective electromagnetic radiation detectors 84 and 86, respectively, and simultaneously, either encouraging, and/or inhibiting the detection of the respective objects of interest and/or products 11, by way of selecting the electromagnetic radiation detectors 84 and 86, respectively so as to improve a contrast which is generated between the respective objects of interest and/or products 11, and the selectively energized, and deenergized background element 30, during the detection of the objects of interest and/or products 11 which are passing through the inspection station 20 (FIG. 8). In the present methodology 10, and after the step of providing the controller 100 (FIG. 9), the method of the present invention further comprises a step 101 of defining a first mode of operation for the controller, and which includes selectively energizing the electromagnetic radiation emitters 35, and which are enclosed within the background element 30, and then simultaneously, and selectively, adjusting (increasing or decreasing) 90 the luminosity or radiance of the respective electromagnetic radiation emitters 35, so as to provide, or generate 102, a resulting, and predetermined, background illumination (FIG. 5). The method 10 includes another step 103 (FIG. 2) of detecting the generated, predetermined, background illumination 102, with at least one of the line scan imaging assembly 81, and/or the first electromagnetic radiation detector 84, and which is further operably coupled with the laser scanner 70. After the step of defining the first mode of operation 101 for the controller, the method 10 further comprises a step 104 of receiving, with the controller, 100, a first, electrical image signal which is generated by the line scan imaging assembly 81, and which identifies the predetermined, background element 30 illumination 102 which is generated, or emitted by the energized electromagnetic radiation emitters 35, and which are enclosed within the background element 30. In this arrangement, other, different, electrical image signals received from the line scan imaging assembly 81 are further identified by the controller 100 as being other objects of interest and/or products, 11, and which are present within the product stream 12, which are further positioned in a given location along the line of sight 26. After the step of providing the first mode of operation 101, for the controller 100, the method further comprises a step 105 (FIG. 2) of receiving, with the controller 100, a second, electrical image signal which is generated by the first, electromagnetic radiation detector 84, and which is further operably coupled with the laser scanner 70. The controller 100 identifies the second electrical image signal as a view or image of the predetermined background illumination 102, and which is emitted by the energized background element 30. Other different, electrical signals which are received from the first, electromagnetic radiation detector 84 are then identified by the controller 100, as being objects of interest and/or products 11 which are present in the product stream 12, and which are further located along the line of sight 26, of the laser scanner 70, and at a location along the line of sight 26 which is indicated by a position of the laser flying spot beam 71 along the line of sight 26.

Figure 4:
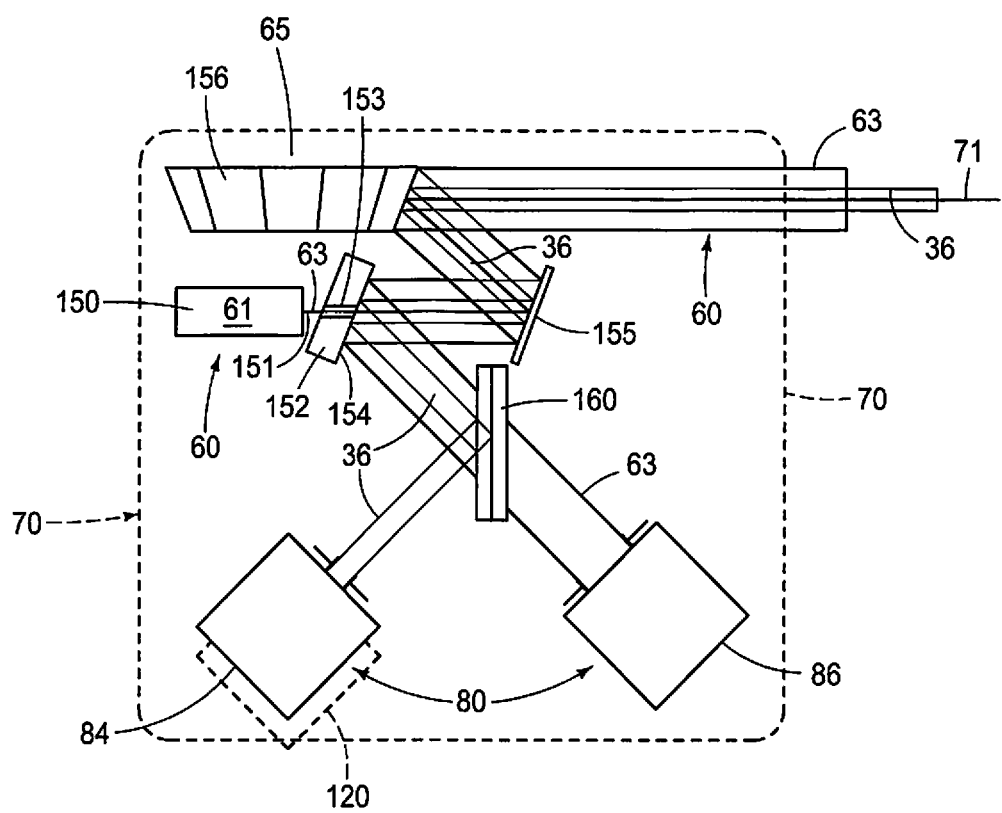
FIG. 4 is a partial, and greatly simplified, side elevation view of the present apparatus, and which implements at least some steps of the methodology of the present invention.
Figure 12:
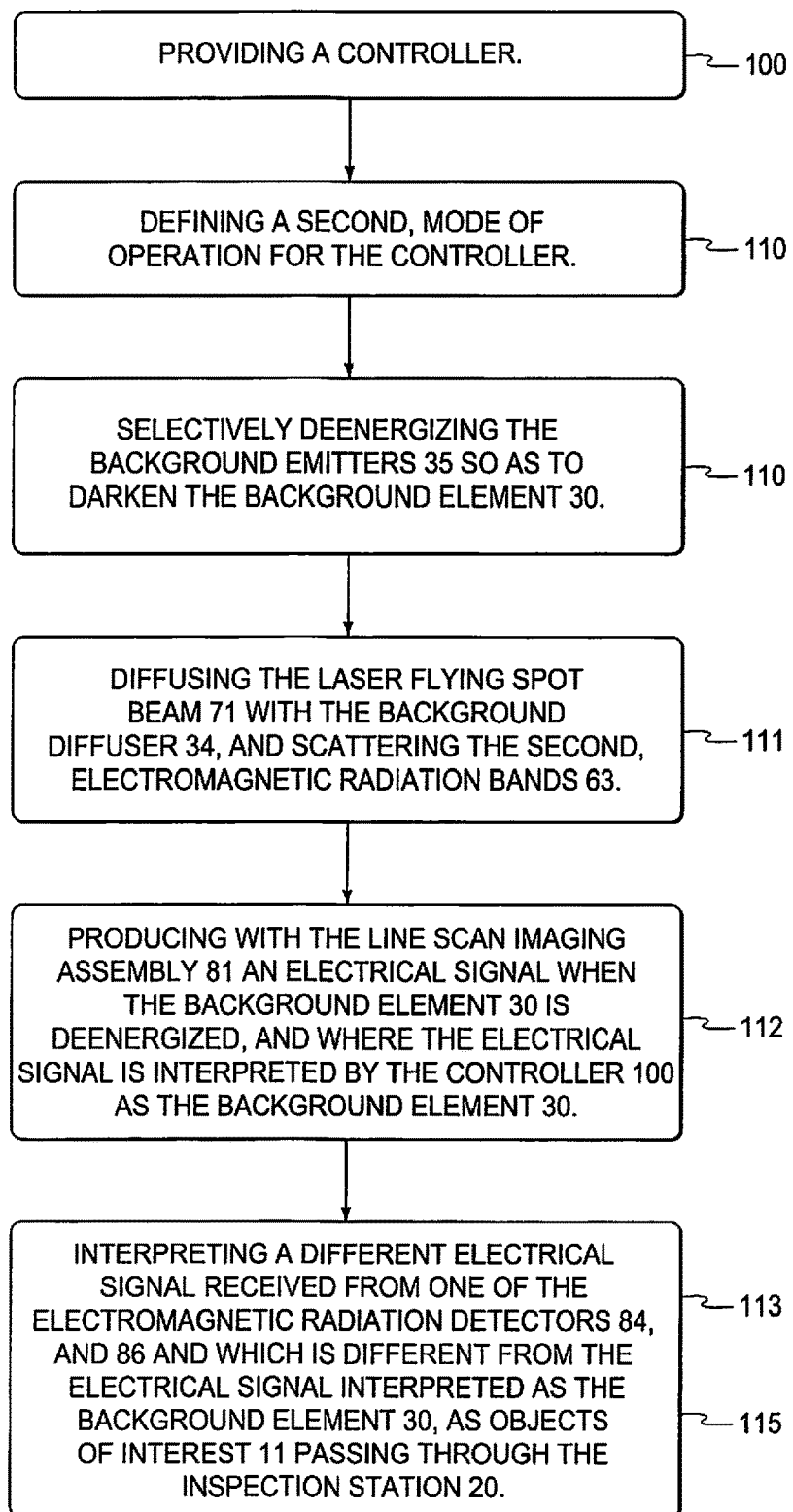
FIG. 12 is a fifth method step flow diagram depicting several additional steps in the methodology of the present invention.
Figure 13:
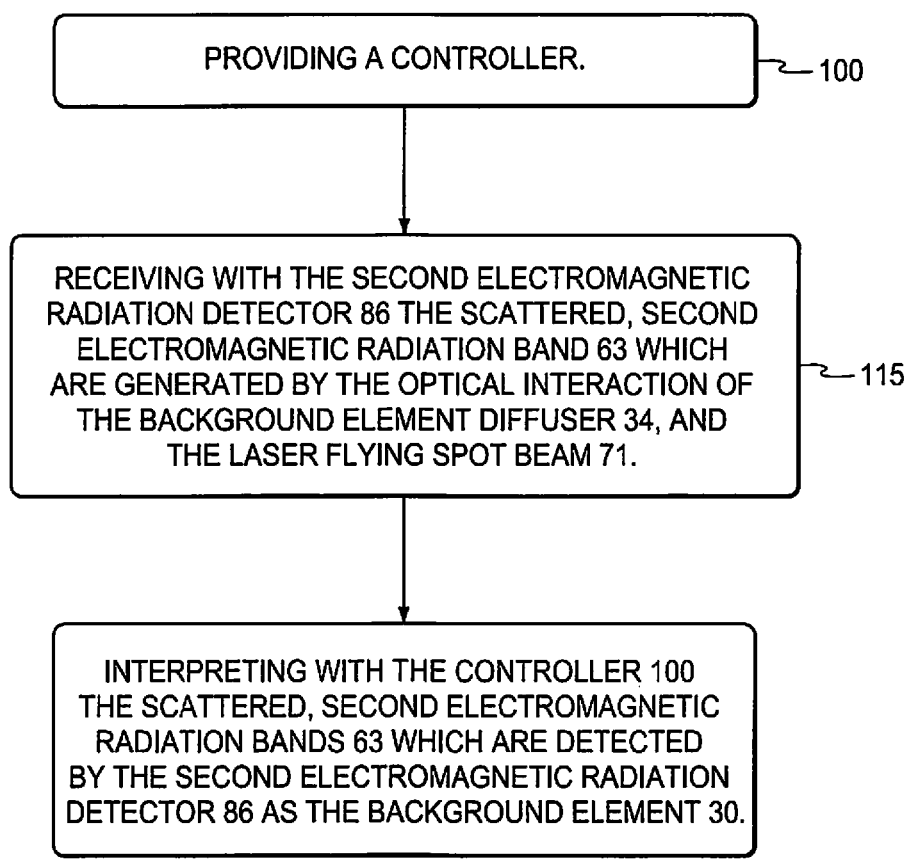
FIG. 13 is a sixth method step flow diagram depicting several additional steps in the methodology of the present invention.

The method of the present invention 10 includes a still further mode of operation for the controller 100. In this regard, the methodology 10 of the present invention defines a second mode of operation 110 (FIG. 12) for the controller 100, and which includes a step of selectively deenergizing the respective electromagnetic radiation emitters 35, and which are located within the background element 30, so as to darken (or make less luminous or radiant) the background element 30. This darkening of the background element is caused by the reduction of, or the absence of any emitted and diffused electromagnetic radiation 102 which is generated by the energized electromagnetic radiation emitters 35. Further, the method 10 includes a still further step 111 of facilitating the diffuse interaction of the electromagnetic radiation diffuser 34, with the laser flying spot beam 71, and which is generated by the laser scanner 70, so as to encourage the diffusing and scattering of the second electromagnetic radiation bands 63 which have been generated. The method 10 includes still another step 112 of producing an electrical signal by means of the line scan imaging assembly 81, when the background element 30 is deenergized. The electrical signal produced in step 112 has a given electrical signal level, and which is subsequently interpreted by the controller 100, as the background element 30. Further, and in the second mode of operation 110, the method includes still another step 113 (FIG. 2) of interpreting the electrical signal received by the controller 100 from at least one of the electromagnetic radiation detectors 84 and 86, respectively, and which is different from the given signal generated when the background element 30 is deenergized, and when the objects of interest and/or products 11 which are located along the line of sight 26 pass through the inspection station 20. The method 10 of the present invention includes another step 114 of receiving, with the second electromagnetic radiation detector 86, the scattered, second, electromagnetic radiation bands 63, and which are generated by an optical interaction of the background element diffuser element 34, with the laser flying spot beam 71. The method 10 includes yet another step 115 (FIG. 1) of interpreting with the controller 100, the scattered, second, electromagnetic radiation bands 63, and which are detected by the second, electromagnetic radiation detector 86, as a background element 30. In this present methodology 10, the second mode of operation 110 includes a step 116 (FIG. 2) of selectively energizing the electromagnetic radiation emitters 35 and 60, with the controller 100, so as to produce given, predetermined wavelengths of electromagnetic radiation 102 (FIGS. 5 and 63 in FIG. 4). Still further, the method 10 includes another step 117 of detecting by one of the other first or second electromagnetic radiation detectors 84 and/or 86, respectively, the given wavelengths of electromagnetic radiation which are emitted in step 116, by the selective energizing of electromagnetic radiation emitters 35.

Figure 11:
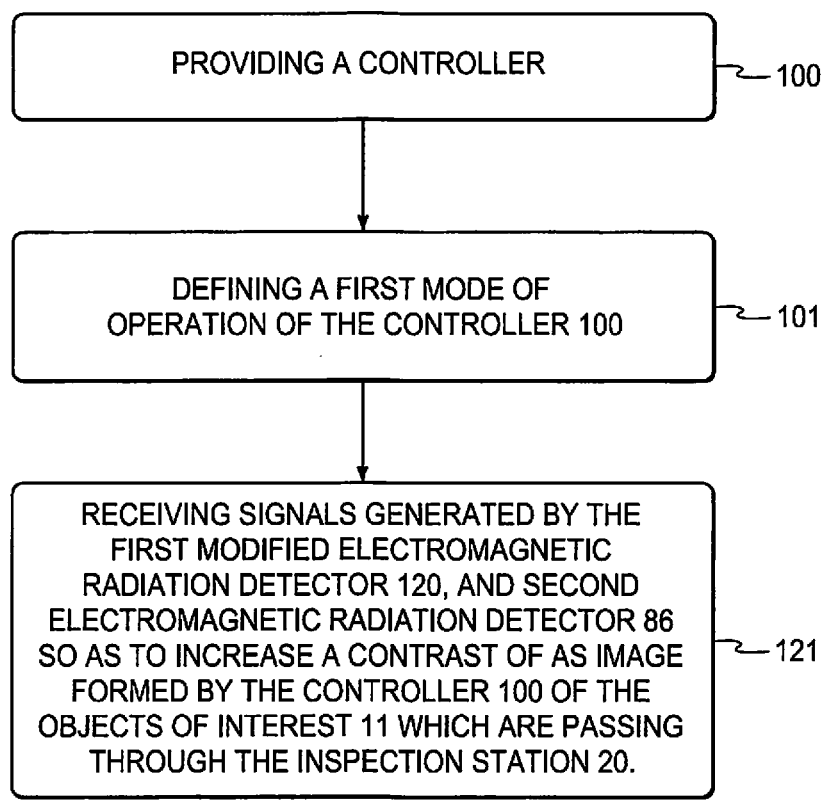
FIG. 11 is a fourth method step flow diagram depicting several additional steps in the methodology of the present invention.

In one possible form of the invention, and as discussed, above, the methodology 10 includes a step 120 (FIG. 2) of providing a first, modified, electromagnetic radiation detector (for example, one that has a telescopic lens, not shown) (FIG. 4), and rendering the first, modified, electromagnetic radiation detector 120 operable to detect the first electromagnetic radiation bands 36, and which are emitted by the background element 30, and which further is transmitted by the optical diffusing action of the electromagnetic radiation diffuser 34. The method 10 includes another step of generating a resulting electrical signal, and wherein the controller 100, during the first mode of operation 101, and upon receiving the electrical signal generated by the first, modified, electromagnetic radiation detector 120, interprets the received signal as a view of the background element 30, and other received, and different electrical signals are interpreted by the controller 100 as being objects of interest and/or products 11 which are located along the line of sight 26 of the laser scanner 70, and at a location which is indicated by a position of the laser flying spot beam 71 which is further oriented along the line of sight 26 (FIG. 11). In the method 10, as described, above, the first mode of operation 101 further comprises a step 121 of receiving, and processing with the controller 100 both of the electrical signals generated by the first, modified, electromagnetic radiation detector 120, and the second, electromagnetic radiation detector 86, so as to increase a contrast of a resulting image which is formed by the controller 100 of the objects of interest and/or products 11, and which are further located along the line of sight 26, and passing through the inspection station 20 (FIGS. 8 and 11). In one possible form of the invention the methodology 10 includes another step 130 (FIG. 2) of selectively energizing, with the controller 100, the multiplicity of selectively energizable, electromagnetic radiation emitters 35, so as to generate predetermined, discreet, wavelength bands of electromagnetic radiation 102; and a subsequent step 131 of sensing at least one of the predetermined, discreet, wavelength bands with the line scan imaging assembly 81, and a second, discreet, wavelength band with the laser scanner 70. In one possible form of the invention 10, the step of moving a product stream 12 which is formed of the individual objects of interest and/or products to be sorted 11 further includes the step of providing a product stream 12 (FIG. 2), and which is formed of the objects of interest and/or products 11 each having a predetermined, spectral and/or scatter response characteristic; and another, second step 130 of selectively energizing, with the controller 100, the electromagnetic radiation emitters 35 which are enclosed within the background element 30 so that the emitted electromagnetic radiation which is generated 102 (FIG. 5) by the energized electromagnetic radiation emitters 35 provides an increased contrast relative to the objects of interest 11 which form the product stream 12, and the background element 30, by, on the one hand, inhibiting the destructive interference of the generated first, second and third electromagnetic radiation bands 36, 63, and 64 respectively, with at least some of the electromagnetic radiation detectors 120, 84 and/or 86; and/or the line scan imaging assembly 81, respectively; and/or, on the other hand, by encouraging the destructive interference of the first, second and third bands of electromagnetic radiation bands 36, 63, and 64, respectively, with at least some of the electromagnetic radiation detectors 120, 84 and 86, and/or line scan imaging assembly 81, respectively, and thereby enhancing the ability of the controller 100 to visibly discern and/or detect the objects of interest and/or products 11 in the product stream 12, and which is passing through the inspection station 20 (FIG. 8). The methodology 10 of the present invention includes a step 124 of providing a selectively actuatable ejector (FIG. 2) which may be rendered operable by the controller 100, so as to remove defective or undesirable objects of interest 14 from the product stream 12, by way of an ejection signal generated by the controller 100, and based, at least in part, upon the electrical signal information provided by at least some of the electromagnetic radiation detectors 84, 86, 120, and the line scan imaging assembly 81.

An apparatus 10 which is operable to achieve the methodology steps as described in the paragraphs, above, is seen in the attached drawings. In this regard the apparatus which is generally indicated by the numeral 10 includes an inspection station 20, and which is further defined, at least in part, by spaced, opposite, first and second sides 23 and 24, respectively. The inspection station, is further defined, at least in part, by an intermediate region 25, (FIG. 2), and which is located between the opposite, spaced, first and second sides. In this arrangement, and as seen in the drawings, a predetermined line of sight 26 (FIG. 1) is defined, or established within the intermediate region. The significance of this intermediate region 25 will be more evident from the discussion, which is provided, below. A background element 30, (FIG. 5) is provided, and which is positioned on the first side 23, of the inspection station 20, and which further comprises a multiplicity of selectively energizable electromagnetic radiation emitters 35, and which, when energized, individually emits a first band of electromagnetic radiation 36 having one or more discreet wavelengths, and which further is emitted in the direction of, and along the line of sight 26, and further towards the second side 24, of the inspection station 20. The background element 30 includes an optically transmissive electromagnetic radiation diffuser element 34, and which is made integral with the background element 30, and which further encloses, at least in part, the multiplicity of selectively energizable electromagnetic radiation emitters 35, and diffuses the first band of electromagnetic radiation 36 which is generated by the enclosed, and energized, electromagnetic radiation emitters 35. The apparatus 10 is operable to inspect a stream of products to be sorted 12, and which are released, and then move, in one form of the invention, under the influence of gravity, through the aforementioned inspection station 20, and along the line of sight 26. The stream of products 12 include at least some products or objects of interest 11 having either acceptable characteristics or features 13; or unacceptable characteristics or product features 14, as well as other objects of interest which are not product related. The products may have, in one form of the invention, given, and predetermined optical or spectral characteristics. The apparatus 10 includes a laser scanner 70, (FIGS. 1 and 2) which when energized, emits a laser flying spot beam 71, and which is formed of a second band 63 of electromagnetic radiation having one or more predetermined wavelengths, and which is further positioned on the second side 24, of the inspection station 20. The laser flying spot beam 71 is repeatedly directed or moved 72 along the line of sight 26, and towards the background element 30, and which is positioned on the first side 23, of the inspection station 20. The second band of electromagnetic radiation 63, and which forms the laser flying spot beam 71 is reflected, at least in part, from any one of the products and/or objects of interest 11 in the product stream 11, and which is passing through the inspection station 20; the background element 30; and from any other objects of interest present in the product stream 12; and/or all of the foregoing. The apparatus 10 includes a first electromagnetic radiation detector 84 which is located on the second side 24, of the inspection station 20, and which is further operationally coupled with the laser scanner 70. The first electromagnetic radiation detector 84 is rendered operable to detect only the wavelengths of the first band of electromagnetic radiation 36, and which are emitted by the background element 30, and which are further diffused by the diffuser element 34, and thereafter generates a corresponding electrical signal 105 (FIG. 2). The apparatus 10 includes a second electromagnetic radiation detector 86, and which is located or positioned on the second side 24, of the inspection station 20, and which is further operationally coupled with laser scanner 70. The second, electromagnetic radiation detector 86 is rendered operable to detect only the wavelengths of the second band of electromagnetic radiation 63, and which are emitted by the laser scanner 70, and which are further reflected from any one of the background element 30; products, or objects of interest 11 which are traveling in the product stream 12, and which are further passing through the inspection station 20, and along the line of sight 26, and/or all of the foregoing. The second, electromagnetic radiation detector 86 further generates a corresponding electrical signal 87. The first electromagnetic radiation detector 84 can be modified to have an aperture which receives electromagnetic radiation which has a small focal region; a telescopic lens which forms a small focal region; or a pin-hole aperture which also achieves a small area of focus. The apparatus 10 includes a line scan imaging assembly 81 which is positioned on the second side 24 of the inspection station 20, and which is further oriented in optical receiving relation relative to the line of sight 26. The line scan imaging assembly 81 operates in combination with a second, partial dichroic mirror 161, and optionally, with a third reflective mirror 162, as earlier described, and which are seen in FIG. 2. The laser scanner further includes a Pritchard mirror 152, and, optionally, a second, reflecting mirror 155, rotating polygon-shaped mirror 156, and first dichroic mirror 160. These structures, working in combination, direct the predetermined wavelengths of electromagnetic radiation returned from the inspection station 20 to the appropriate electromagnetic radiation detectors 84, and 86, respectively (FIG. 2). The line scan imaging assembly 81 receives, and detects the first band of electromagnetic radiation 36, and which is emitted by the background element 20, and which further is then diffused by the diffuser element 34. The apparatus 10 includes one or more selectively energizable radiators 62, which when energized, emits a third band of electromagnetic radiation 64, having one or more predetermined wavelengths, and which further illuminates the line of sight 26, and the stream of products 12 which may include other objects of interest passing through the inspection station 20, and along the line of sight 26. The line scan imaging assembly 81, forms or generates an electrical signal which represents an image of the product stream 12 which is passing through the inspection station 20, and along the line of sight 26. The apparatus 10 further includes a controller 100 which is operably and controllably coupled to each of the background element 30; laser scanner 70; first and second electromagnetic radiation detectors 84 and 86, respectively; line scan imaging assembly 81; and selectively energizable radiators 61 and 62, and which further receives and processes the electrical signals generated by each of the first and second electromagnetic radiation detectors 84 and 86, respectively, and the electrical image signals generated by the line scan imaging assembly 81. The controller 100 selectively energizes the respective background element 30; laser scanner 70; radiators 61 and 62; and/or line scan imaging assembly 81, so as to improve the detection of the individual products and/or other objects of interest 11 moving in the product stream 12, by increasing the contrast of the respective products and/or objects of interest 11, in at least some of the electrical image signals processed by the controller 100 as the product stream 12, having the products and/or objects of interest 11 pass through the inspection station 20.

The apparatus 10 of the present invention, in one possible form, possesses or includes a multiplicity of selectively energizable electromagnetic radiation emitters 35, and which are enclosed within the background element 30. These individual emitters 35, when selectively energized by the controller 100, may emit more than one discreet bandwidth of visible and/or invisible electromagnetic radiation which is included within the emitted first band of electromagnetic radiation 36. The apparatus 10, as disclosed further includes a controller 100 which is operable to selectively increase and decrease the luminosity or radiance 90 (FIG. 5) of the respective, energized electromagnetic radiation emitters 35, and which are enclosed within the background element 30; and the one or more selectively energizable radiators 61 and 62. As should be understood, the one or more first bands of emitted electromagnetic radiation 36 have wavelengths which can be similar to the wavelengths of the second and/or third bands of electromagnetic radiation, and which are identified by the numerals 63 and 64, respectively. In one possible form of the invention, the first band of electromagnetic radiation 36 has wavelengths which can be dissimilar from the wavelengths of the second and/or third bands of electromagnetic radiation 63 and 64, respectively. In still another possible form of the invention, the line scan imaging assembly 81 includes multiple line scan imaging assemblies 91 (FIG. 1). In yet another possible form of the invention 10, the line scan imaging assembly 81 is oriented so as to view or image an outwardly facing surface 33 of the electromagnetic radiation diffuser element 34, and which is positioned on the first side 23, of the inspection station 20. In one form of the invention, the laser scanner 70 has a predetermined viewing orientation 92 (FIGS. 1, 2 and 3) relative to the line of sight 26, and the background element 30, respectively. In one possible form of the invention the line scan imaging assembly 81 may have a viewing orientation 92 which is the same as the laser scanner 70 (FIGS. 1,2,3, and 7) In another possible form of the invention (FIGS. 6 and 7) the laser scanner 70 has a predetermined viewing orientation 93, relative to the line of sight 26, and the background element 30, respectively, and which is different from that of the line scan imaging assembly 81.

The apparatus 10 of the present invention, in one possible form, includes an arrangement, and wherein the selectively energizable radiator 62 has a predetermined spatial orientation with respect to the inspection station 20, and which further facilitates the illumination of the line of sight 26, with the third band of electromagnetic radiation 64, and simultaneously, substantially avoids an illumination of the background element 30 with the same third band of electromagnetic radiation 64 (FIG. 2). In one possible form of the invention 10 the controller 100, in the first mode of operation 101 (FIG. 9) selectively energizes the respective electromagnetic radiation emitters 35 which are enclosed within the background element 30, and further simultaneously, and selectively, adjusts 90 (FIG. 5) the luminosity or radiance of the respective energized electromagnetic radiation emitters 35 so as to provide a resulting and predetermined background illumination 102 which can be detected by each of the line scan imaging assembly 81, and the first electromagnetic radiation detector 84 which is operably coupled with the laser scanner 70 (FIG. 2). In another form of the invention 10, the controller 100, in a first mode of operation 101 (FIG. 9), and upon receiving an electrical signal generated by the line scan imaging assembly 81, and which indicates the predetermined background illumination 102 (FIG. 5) emitted by the background 30, interprets 104 (FIG. 2) the received electrical signal as a view of the background 30. In this form of the invention 10 other different electrical signals received from the line scan imaging assembly 81 are then interpreted by the controller 100, as being products or objects of interest 11 which are positioned in a given location along the line of sight 26. In one possible form of the invention the controller 100, in the first mode of operation 101 (FIG. 9), and upon receiving 105 an electrical signal from the first electromagnetic radiation detector 84, and which is operably coupled to the laser scanner 70, interprets the received electrical signal as a view of the predetermined background illumination 102 (FIG. 5) which is emitted by the background element 30. In this form of the invention other different electrical signals received from the first electromagnetic radiation sensor 84 (FIG. 2) are interpreted by the controller 100 as being products or objects of interest 11 which are located along the line of sight 26, of the laser scanner 70, and at a location which is indicated by a position of the laser flying spot beam 71 along the line of sight 26 (FIG. 1). In another form of the invention the apparatus 10 includes a first, modified electromagnetic radiation detector 120 (FIG. 4) which has been rendered operable to detect the wavelengths of the first band of electromagnetic radiation 36, and which is transmitted by the background element 30, but which is caused or effected by the electromagnetic radiation diffuser element 34, and then forms a corresponding electrical signal. In this form of the invention the controller 100, in the first mode of operation 101 (FIG. 9), and upon receiving 121 the electrical signal from the first, modified, electromagnetic radiation detector 120 interprets the received electrical signal as a view of the background element 130. In this form of the invention other different electrical signals are interpreted by the controller 100 as being products, or objects of interest and/or products 11 which are located along the line of sight 26 of the laser scanner 70, and at a location which is indicated by a position of the laser flying spot beam 71, along the line of sight 26 (FIG. 1). The controller 100, in the first mode of operation 101 (FIG. 9), receives and processes both the electrical signals from the first, modified electromagnetic radiation detector 120, and the second electromagnetic radiation detector 86 so as to increase a contrast of a resulting image formed by the controller 100 of the line of sight 26, and improve the detection of the products and/or objects of interest 11 which are passing through the inspection station 20 (FIG. 8).

In another form of the invention 10, the controller 100, in a second mode of operation 110 (FIG. 12), selectively deenergizes the electromagnetic radiation emitters 35 which are enclosed within the background element 30, and thereby causes the background element 30 to appear darkened, or less radiant, to the respective electromagnetic radiation detectors 80 because of the absence of any emitted background illumination 102 which is generated by the de-energized electromagnetic radiation emitters 35 (FIG. 5). In this operational condition, the electromagnetic radiation diffuser 34 is operable to optically interact with the laser flying spot beam 71, and which is formed of the one or more second bands of electromagnetic radiation 63, so as to diffuse, and scatter, the one or more second bands of electromagnetic radiation 63. The electrical signal produced by the line scan imaging assembly 81, when the background element is deenergized, has a given electrical signal level which is interpreted 115 by the controller 100 as the deenergized background element 30. Electrical signals which are received by the controller 100, and which are further different from the given electrical signal level generated by the deenergized background element 30, are subsequently interpreted by the controller 100 as products or objects of interest 11 which are positioned along the line of sight 26. In the operational arrangement as discussed, above, the second, electromagnetic radiation detector 86 receives the scattered, second band of electromagnetic radiation 63 from the deenergized background element 30, and the controller 100 interprets the scattered, second band of electromagnetic radiation 63 which is detected by the second electromagnetic radiation detector 86 as the background element 30.

In one form of the invention 10 the apparatus, as described, further includes a first, modified electromagnetic radiation detector 120, and which has been rendered operable to sense the first band of electromagnetic radiation 36, and which has been transmitted by the diffuser element 34, and then forms a corresponding electrical signal which has been given an electrical signal level. The controller 100 then interprets the sensing of the transmitted, first source of electromagnetic radiation 36 by the first, modified electromagnetic radiation detector 120 (FIG. 4), and the scattered, second source of electromagnetic radiation 63, by the second, electromagnetic radiation detector 86, at the given electrical signal levels as the background 30. The controller 100 then interprets other, different and received electrical signal levels as indicating the presence of products or objects of interest 11 within the field of view 26, and at a location which is correlated with a position of the laser flying spot beam 71, along the line of sight 26. In the multiple possible forms of the invention as described herein, the controller 100 selectively energizes the multiplicity of selectively energizable electromagnetic radiation emitters 35 so as to emit given wavelengths of electromagnetic radiation which may, on the one hand, not be detected by the second electromagnetic radiation detectors 86, or which is a scattering caused by the electromagnetic radiation diffuser 34 of the wavelengths of the second band of electromagnetic radiation 63 and which is emitted by the first electromagnetic radiation emitters 61, and which are further coupled to the laser scanner 70; or on the other hand, which may be detected by the first electromagnetic radiation detector 84, or the modified, electromagnetic radiation detector 120 which detects the first radiation band 36, as transmitted by the electromagnetic radiation diffuser element 34, either selectively, and independently or simultaneously, and in conjunction with the detection of a scattering caused by the electromagnetic radiation diffuser element 34 of the wavelengths of the second band of electromagnetic radiation 63 which is emitted by the first electromagnetic radiator 61, and which is operably coupled to the laser scanner 70. In either of the aforementioned scenarios, described, above, the line scan imaging assembly 81 may detect the first radiation bands 36, as transmitted by the electromagnetic radiation diffuser element 34, either selectively, and independently, or simultaneously, and in conjunction with the detection of the background element 30, by either or both of the first electromagnetic radiation detector 84, or alternately, by the modified, first electromagnetic radiation detector 120, and the second, electromagnetic radiation detector 86 (FIG. 4). Simultaneous operation, and detection is possible because of the multiplicity of selectively energizable electromagnetic radiation emitters 35, and the one or more selectively energizable radiators 61 and 62, and which further may be selected to generate or emit similar or dissimilar wavelength bands, and because the invention 10 can, by way of the controller 100, selectively avoid or make use of destructive optical interference to improve a resulting contrast which is generated or created between the respective objects of interest and/or products 11, and the energized and/or deenergized background element 30. In one possible form of the invention, the controller 100 selectively energizes the multiplicity of selectively energizable electromagnetic radiation emitters 35 so as to emit predetermined, discreet wavelength bands of electromagnetic radiation which are sensed as one, predetermined, discreet wavelength band by the line scan imaging assembly 81; and a second discreet wavelength band by the laser scanner 70. In another possible form of the invention the respective products and objects of interest 11 each have a predetermined spectral and/or scatter response characteristic. In this arrangement the controller 100 selectively energizes at least some of the electromagnetic radiation emitters 35, and which are enclosed within the background element 30, so that the emitted electromagnetic radiation (second and third bands 63 and 64), and the first band of electromagnetic radiation 36 which forms the predetermined background illumination 102 that is generated by the background element 30, provides an increased contrast relative to the products and/or objects of interest 11 which are passing through the inspection station 20, and which increases the ability of the laser scanner 70; line scan imaging assembly 81; and controller 100; to detect the products and/or the objects of interest 11 in the product stream 12, and which is passing through the inspection station 20.

Therefore it will be seen that the present invention provides a very convenient and novel means for viewing, identifying, and then sorting objects of interest and/or other products provided in a given product stream.

In compliance with the statute, the invention has been described in language more or less specific as to structural and methodical features. It is to be understood, however, that the invention is not limited to the specific features shown and described since the means herein disclosed comprise preferred forms of putting the invention into effect. The invention is, therefore, claimed in any of its forms or modifications within the proper scope of the appended claims appropriately interpreted in accordance with the Doctrine of Equivalence.

We claim:
1. A method for sorting, comprising:
   moving a product stream formed of individual objects of interest to be sorted through an inspection station;
   selectively energizing a background element which is located adjacent to the inspection station, so as to generate discrete, first electromagnetic radiation bands, and directing the discrete, first electromagnetic radiation bands towards the moving product stream passing through the inspection station;
   energizing, in a selective manner, at least one radiator which is located adjacent to the inspection station so as to individually generate a discrete, second electromagnetic radiation band, and directing the second, discrete, electromagnetic radiation band towards the moving product stream passing through the inspection station;
   positioning adjacent to the inspection station individual electromagnetic radiation detectors for detecting the first and second, discrete, electromagnetic radiation bands which are emitted, and either reflected by the objects of interest to be sorted; or generated by the background element when the background element is energized; or is reflected from the background element; and
   controllably coupling a controller to each of the selectively energizable radiators; selectively energizable background element; and the respective electromagnetic radiation detectors, and selectively optimizing the energizing and operation of each of the radiators, background element, and electromagnetic radiation detectors, in real-time, and by way of the controller, while detecting the objects of interest with the respective electromagnetic radiation detectors, and simultaneously, either encouraging and/or inhibiting the detection of the respective objects of interest by at least some of the electromagnetic radiation detectors so as to improve a contrast generated between the respective objects of interest, and the energized and deenergized background element, during the detection of the objects of interest which are passing through the inspection station.

2. A method as claimed in claim 1, and wherein the inspection station has opposite, first and second sides, and wherein the method further includes a step of establishing a line of sight which is defined between, and is parallel to, the opposite, first and second sides of the inspection station, and which further passes through the product stream.

3. A method as claimed in claim 2, and wherein the step of energizing, in a selective manner, a plurality of radiators so as to individually generate the discrete second, and a third electromagnetic radiation bands, and which further comprises:
   providing, and then positioning, individual radiators on the second side of the inspection station, and which generate individual bands of electromagnetic radiation having predetermined wavelengths which are directed along the line of sight; and
   operably coupling at least one of the electromagnetic radiation detectors with at least one of the individual radiators.

4. A method as claimed in claim 3, and wherein the step of energizing, in a selective manner a plurality of radiators further comprises:
   generating one or more visible or invisible electromagnetic bands of radiation either simultaneously and/or sequentially.

5. A method as claimed in claim 4, and wherein the step of selectively energizing the background element further comprises:
   selectively generating one or more visible or invisible electromagnetic radiation bands either simultaneously and/or sequentially;
   positioning the background element on the first side of the inspection station; and
   directing the generated, first electromagnetic radiation bands, in the direction of the opposite, second side of the inspection station.

6. A method as claimed in claim 5, and wherein the step of positioning the background element on the first side of the inspection station further comprises:
   providing a background element which has both an optically transmissive electromagnetic radiation diffuser element, and further defines an internal cavity;
   operably positioning a multiplicity of selectively energizable electromagnetic radiation emitters within the internal cavity of the background element;
   operably coupling the respective electromagnetic radiation emitters positioned within the internal cavity of the background element with the controller;
   selectively energizing the respective electromagnetic radiation emitters located within the internal cavity of the background element with the controller, either simultaneously and/or sequentially; and
   diffusing the electromagnetic radiation which is emitted by the energized electromagnetic radiation emitters with the optically transmissive electromagnetic radiation diffuser element.

7. A method as claimed in claim 6, and wherein the step of selecting, and then positioning the individual radiators on the second side of the inspection station further comprises:
   providing a laser scanner, and positioning the laser scanner on the second side of the inspection station;
   selectively energizing the laser scanner with the controller so as to produce a laser flying spot beam which is formed of one or more visible or invisible, second electromagnetic radiation bands, and repeatedly moving the flying spot beam along the line of sight, and illuminating the product stream which is moving through, and between, the first and second sides of the inspection station, and further in the direction of the background element which is positioned on the first side of the inspection station;
   operably coupling at least two of the electromagnetic radiation detectors with the laser scanner; and
   detecting, with the at least two electromagnetic radiation detectors, the first electromagnetic radiation bands generated by the energized background element, and the second electromagnetic radiation bands generated by the energized laser scanner, and which are reflected by the objects of interest moving along in the product stream.

8. A method as claimed in claim 7, and wherein the step of positioning adjacent to the inspection station individual electromagnetic radiation detectors further comprises:
   providing a line scan imaging assembly, and positioning the line scan imaging assembly on the second side of the inspection station, and orienting the line scan imaging assembly in optical receiving relation relative to the line of sight; and
   operably and controllably coupling the line scan imaging assembly with the controller.

9. A method as claimed in claim 8, and wherein the step of selecting, and then positioning the individual radiators on the second side of the inspection station further comprises:

providing a selectively energizable radiator which is positioned so as to illuminate, when energized, the line of sight, and the stream of products moving within the inspection station, with the third band of electromagnetic radiation, as the product stream passes along the line of sight.

10. A method as claimed in claim 9, and wherein the step of operably coupling at least two electromagnetic radiation detectors with the laser scanner further comprises:

providing a first electromagnetic radiation detector which is positioned on the second side of the inspection station, and which is further operably coupled with the laser scanner;

detecting with the first electromagnetic radiation detector the first electromagnetic radiation bands which are generated by the energized electromagnetic radiation emitters which are enclosed within the internal cavity of the background element, and which are further diffused by the diffuser element;

providing a second electromagnetic radiation detector which is positioned on the second side of the inspection station, and which is further operably coupled with the laser scanner; and detecting with the second, electromagnetic radiation detector, the second electromagnetic radiation bands which are emitted by the energized laser scanner, and which are further reflected from at least one of the objects of interest travelling in the product stream, and passing simultaneously through the inspection station, and along the line of sight.

11. A method as claimed in claim 10, and wherein the step of controllably coupling the controller to at least one selectively energizable radiator; the selectively energizable background element; and the respective electromagnetic radiation detectors further comprises:

selectively increasing and decreasing the radiance of the energized electromagnetic radiation emitters which are located within the internal cavity of the background element, and which is further positioned on the first side of the inspection station; and the selectively energizable radiators which are located on the second side of the inspection station.

12. A method as claimed in claim 11, and wherein the first electromagnetic radiation bands have given wavelengths which are similar to the wavelengths of the second and/or third bands of electromagnetic radiation.

13. A method as claimed in claim 11, and wherein the first electromagnetic radiation bands have given wavelengths which are dissimilar to the wavelengths of the second, and/or third bands of electromagnetic radiation.

14. A method as claimed in claim 8, and wherein the step of providing a line scan imaging assembly further comprises:

providing multiple line scan imaging assemblies, and positioning each of the line scan imaging assemblies so as to view the diffuser element which forms, at least in part, a portion of the background element.

15. A method as claimed in claim 11, and wherein the steps of providing the laser scanner and line scan imaging assembly further comprises:

positioning each of the laser scanner, and line scan imaging assembly, so as to have a similar viewing orientation relative to the line of sight.

16. A method as claimed in claim 11, and wherein the steps of providing the laser scanner and line scan imaging assembly further comprises:

positioning each of the laser scanner and line scan imaging assembly so as to have a dissimilar viewing orientation relative to the line of sight.

17. A method as claimed in claim 9, and wherein the step of providing a selectively energizable radiator which generates a third band of electromagnetic radiation further comprises:

positioning the selectively energizable radiator which generates the third band of electromagnetic radiation in a predetermined spatial orientation relative to the inspection station so as to illuminate the line of sight with the third band of electromagnetic radiation, while simultaneously inhibiting an illumination of the background element with the third band of electromagnetic radiation.

18. A method as claimed in claim 11, and wherein after the step of providing the controller, the method further comprises:

defining a first mode of operation for the controller which includes selectively energizing the electromagnetic radiation emitters which are enclosed within the background element, and simultaneously, and selectively adjusting the radiance of the respective electromagnetic radiation emitters so as to provide a resulting and predetermined background illumination; and detecting the predetermined background illumination with at least one of the line scan imaging assembly, and/or the first electromagnetic radiation detector, and which is further operably coupled with the laser scanner.

19. A method as claimed in claim 18, and wherein after the step of defining the first mode of operation for the controller, the method further comprises:

receiving, with the controller, a first electrical image signal which is generated by the line scan imaging assembly, and which identifies the predetermined background element illumination emitted by the energized background element, and wherein other, different, electrical image signals received from the line scan imaging assembly are further identified by the controller as being objects of interest present within the product stream, and which are positioned in a given location along the line of sight.

20. A method as claimed in claim 19, and wherein after the step of providing the first mode of operation for the controller, the method further comprises:

receiving, with the controller, a second electrical image signal generated by the first, electromagnetic radiation detector, and which is operably coupled with the laser scanner, and wherein the controller identifies the second electrical image signal as a view of the predetermined background illumination emitted by the background element, and wherein other, different, electrical signals received from the first electromagnetic radiation sensor are identified by the controller as being objects of interest present in the product stream, and which are further located along the line of sight of the laser scanner, and at a location along the line of sight which is indicated by a position of the laser flying spot beam along the line of sight.

21. A method as claimed in claim 20, and wherein the step of positioning adjacent to the inspection station electromagnetic radiation detectors further comprises:

providing a first, modified, electromagnetic radiation detector, and rendering the first, modified, electromagnetic radiation detector operable to detect the wavelengths of the first electromagnetic radiation bands which are emitted by the background element, and which are transmitted by the electromagnetic radiation diffuser, and further, generating a resulting electrical signal, and wherein the controller, during the first mode of operation, and upon receiving the electrical signal generated by the first, modified electromagnetic radiation detector, interprets the received signal as a view of the background element, and wherein other, different electrical signals, are interpreted, by the controller, as being objects of interest which are located along the line of sight of the laser scanner, and at a location which is indicated by a position of the laser flying spot beam which is located along the line of sight.

22. A method as claimed in claim 21, and wherein the step of defining the first mode of operation further comprises:
receiving and processing, with the controller, both of the signals generated by the first, modified electromagnetic radiation detector, and the second electromagnetic radiation detector so as to increase a contrast of an image formed by the controller of the objects of interest located along the line of sight, and passing through the inspection station.

23. A method as claimed in claim 22, and wherein after the step of defining a first mode of operation for the controller, the method further comprises:
defining a second mode of operation for the controller which includes selectively deenergizing the electromagnetic radiation emitters which are located within the background element so as to darken the background element because of the absence of any emitted, and diffused background illumination;
facilitating the diffuse interaction of the electromagnetic radiation diffuser with the laser flying spot beam generated by the laser scanner, so as to encourage the diffusing, and scattering, of the second electromagnetic radiation bands;
producing an electrical signal by the line scan imaging assembly, and which has a given electrical signal level, and which is subsequently interpreted by the controller as the background element; and
interpreting an electrical signal received by the controller from at least one of the electromagnetic radiation detectors, and which is different from a given signal generated when the background element is deenergized, as objects of interest located along the along the line of sight, and passing through the inspection station.

24. A method as claimed in claim 23, and wherein the method further comprises the steps of:
receiving with the second electromagnetic radiation detector the scattered, second electromagnetic radiation bands which are generated by an optical interaction of the background element diffuser element with the laser flying spot beam; and
interpreting, with the controller, the scattered, second, electromagnetic radiation bands detected by the second electromagnetic radiation detector as a darkened, deenergized, background element.

25. A method as claimed in claim 24, and further comprising:
selectively energizing the multiplicity of selectively energizable electromagnetic radiation emitters with the controller so as to emit given wavelengths of electromagnetic radiation; and
detecting, by one, or the other of the first or second electromagnetic radiation detectors, the given wavelengths of electromagnetic radiation which are emitted.

26. A method as claimed in claim 25, and further comprising:
selectively energizing, with the controller, the multiplicity of selectively energizable electromagnetic radiation emitters so as to generate predetermined, discreet, wavelength bands of electromagnetic radiation; and
sensing at least one of the predetermined, discreet, wavelength bands with the line scan imaging assembly, and a second, discreet wavelength band with the laser scanner.

27. A method as claimed in claim 26, and wherein the step of moving a product stream formed of individual objects of interest to be sorted further comprises:
providing a product stream formed of objects of interest each having a predetermined spectral and/or scatter response characteristic; and
selectively energizing, with the controller, the electromagnetic radiation emitters which are enclosed within the background element so that the emitted electromagnetic radiation generated by the energized electromagnetic radiation emitters provides an increased contrast relative to the objects of interest forming the product stream, and the background element, by inhibiting the destructive interference of the generated first and second electromagnetic radiation bands with at least some of the electromagnetic radiation detectors, and/or by encouraging the destructive interference of the generated first and second electromagnetic radiation bands with at least some of the electromagnetic radiation detectors, and thereby enhancing the ability of the controller to detect the objects of interest in the product stream passing through the inspection station.

28. A method for sorting, comprising:
providing an inspection station having spaced, opposite sides, and a line of sight is defined between, and is parallel to, the opposite, first and second sides;
providing a background element, and positioning the background element on the first side of the inspection station, and wherein the background element has a multiplicity of selectively energizable electromagnetic emitters which emit a first band of electromagnetic radiation when energized, and which further has an optically transmissive, electromagnetic radiation diffuser element which encloses, at least in part, the multiplicity of selectively energizable electromagnetic radiation emitters;
supplying a stream of products to be sorted, and releasing the stream of products, under the influence of gravity, for movement through the inspection station, and through, and along the line of sight;
positioning a laser scanner on the second side of the inspection station, and selectively energizing the laser scanner so as to emit a laser flying spot beam formed of a second band of electromagnetic radiation having predetermined wavelengths, and wherein the laser flying spot beam is repeatedly directed along the line of sight, and toward the background element which is positioned on the first side of the inspection station;
providing a first electromagnetic radiation detector which is located on the second side of the inspection station, and operationally coupling the first electromagnetic radiation detector with the laser scanner;
providing a second electromagnetic radiation detector which is located on the second side of the inspection station, and operationally coupling the second electromagnetic radiation detector with the laser scanner;

providing a line scan imaging assembly, and positioning the line scan imaging assembly on the second side of the inspection station, and further orienting the line scan imaging assembly in optical receiving relation relative to the line of sight;

providing a radiator, and selectively energizing the radiator so as to emit a third band of electromagnetic radiation having predetermined wavelengths, and which illuminates the line of sight, and the stream of products passing through the inspection station; and controllably and operably coupling a controller to each of the background element; laser scanner; first and second electromagnetic radiation detectors; line scan imaging assembly; and selectively energizeable radiator, and which further selectively energizes the respective background element; laser scanner; radiator; and/or line scan imaging assembly so as to improve the detection of the individual objects of the stream of products, and/or other objects of interest travelling in the product stream, by increasing the contrast of the respective products, and/or objects of interest, in a multiplicity of electrical image signals received by the controller, as the product stream, having the products, or objects of interest, pass through the inspection station.

29. An apparatus for sorting, comprising:

an inspection station having spaced, opposite, first and second sides, and a line of sight is defined between, and is parallel to, the opposite, first and second sides;

a background element positioned on the first side of the inspection station, and having a multiplicity of selectively energizable electromagnetic emitters, and an optically transmissive, electromagnetic radiation diffuser element which encloses, at least in part, the multiplicity of selectively energizable electromagnetic radiation emitters, and which further, when energized, emits predetermined first, electromagnetic radiation bands;

a stream of products to be sorted, and which are released, under the influence of gravity, for movement through the inspection station, and through the line of sight;

a laser scanner positioned on the second side of the inspection station, and which, when energized, emits a laser flying spot beam formed of a second band of electromagnetic radiation having predetermined wavelengths, and wherein the laser flying spot beam is repeatedly directed along the line of sight, and toward the background element which is positioned on the first side of the inspection station;

a first electromagnetic radiation detector which is located on the second side of the inspection station, and which is further operationally coupled with the laser scanner;

a second electromagnetic radiation detector which is located on the second side of the inspection station, and which is further operationally coupled with the laser scanner;

a line scan imaging assembly positioned on the second side of the inspection station, and which is further oriented in optical receiving relation relative to the line of sight;

a selectively energizable radiator which, when energized, emits a third band of electromagnetic radiation having predetermined wavelengths, and which illuminate the line of sight, and the stream of products passing through the inspection station, and along the line of sight; and a controller operably, and controllably coupled to each of the background element; laser scanner; first and second electromagnetic radiation detectors; line scan imaging assembly; and selectively energizeable radiator, and which selectively energizes the respective background element; laser scanner; radiator; and/or line scan imaging assembly so as to improve the detection of the individual objects of the stream of products, and other objects of interest in the product stream, by increasing the contrast of the respective products, and/or objects of interest in a processed electrical image signal which is generated by the first and second electromagnetic radiation detectors, and line scan imaging assembly, as the product stream having the products, or objects of interest pass through the inspection station.

30. An apparatus for sorting, comprising:

an inspection station having spaced, opposite, first and second sides, and which further defines an intermediate region located between the opposite, spaced, first and second sides, and wherein a line of sight is defined within the intermediate region, and is further disposed in substantially parallel relation relative to the opposite, first and second sides;

a background element positioned on the first side of the inspection station and which comprises a multiplicity of selectively energizable electromagnetic emitters, and which, when energized, individually emits a first band of electromagnetic radiation having discreet wavelengths, and which further is emitted in the direction of the line of sight, and towards the second side of the inspection station; and an optically transmissive, electromagnetic radiation diffuser element which is made integral, at least in part, with the background element, and which further encloses, at least in part, the multiplicity of selectively energizable electromagnetic radiation emitters, and further diffuses the first band of electromagnetic radiation which is generated by the enclosed, electromagnetic radiation emitters;

a stream of products to be sorted, and which are released, under the influence of gravity, for movement through the inspection station, and along the line of sight, and wherein the stream of products include at least some products having either acceptable, or unacceptable product features, as well as other objects of interest;

a laser scanner, which when energized, emits a laser flying spot beam formed of a second band of electromagnetic radiation having predetermined wavelengths, and which is further positioned on the second side of the inspection station, and wherein the laser flying spot beam is repeatedly directed along the line of sight, and toward the background element which is positioned on the first side of the inspection station, and wherein the second band of electromagnetic radiation forming the laser flying spot beam is reflected from any one of the products in the product stream passing through the inspection station; the background element; an object of interest present in the product stream; and/or all of the foregoing;

a first electromagnetic radiation detector which is located on the second side of the inspection station, and which is further operationally coupled with the laser scanner, and wherein the first electromagnetic radiation detector is rendered operable to detect only the wavelengths of the first band of electromagnetic radiation which is emitted by the background element, and diffused by the diffuser element, and generates a corresponding electrical signal;

a second electromagnetic radiation detector which is located on the second side of the inspection station, and which is further operationally coupled with the laser scanner, and wherein the second electromagnetic radiation detector is rendered operable to detect only the wavelengths of the second band of electromagnetic radiation which are emitted by the laser scanner, and which are further reflected from the background or diffuser element, and/or any one of the products or objects of interest traveling in the product stream, and which are further passing through the inspection station, and along the line of sight, and which further generates a corresponding electrical signal;

a line scan imaging assembly positioned on the second side of the inspection station, and which is further oriented in optical receiving relation relative to the line of sight, and wherein the line scan imaging assembly receives, and detects the first band of electromagnetic radiation which is emitted by the background element, and which is then diffused by the diffuser element, and wherein the line scan imaging assembly forms an electrical image signal which represents an image of the product stream passing through the inspection station, and along the line of sight;

a selectively energizable radiator which, when energized, emits a third band of electromagnetic radiation having predetermined wavelengths which illuminate the line of sight, and the stream of products which may include other objects of interest passing through the inspection station, and along the line of sight; and a controller operably, and controllably coupled to each of the background element; laser scanner; first and second electromagnetic radiation detectors; line scan imaging assembly; and selectively energizeable radiator, and which further receives, and processes the electrical signals generated by each of the first and second electromagnetic radiation detectors, and the electrical image signal generated by the line scan imaging assembly, and wherein the controller selectively energizes the respective background element; laser scanner; radiator; and/or line scan imaging assembly so as to improve the detection of the individual objects of the stream of products, and other objects of interest in the product stream, by increasing the contrast of the respective products, and the objects of interest in the electrical image signals processed by the controller as the product stream having the products, or objects of interest pass through the inspection station.

31. An apparatus for sorting as claimed in claim 30, and wherein the multiplicity of selectively energizable electromagnetic radiation emitters which are enclosed within the background element, when selectively energized by the controller, emit more than one discrete bandwidth of visible or invisible electromagnetic radiation which is included within the first band of electromagnetic radiation.

32. An apparatus for sorting as claimed in claim 30, and wherein the controller is operable to selectively increase, and decrease the radiance of the energized electromagnetic radiation emitters which are enclosed within the background element;

and the selectively energizable radiator.

33. An apparatus for sorting as claimed in claim 32, and wherein the first band of electromagnetic radiation has wavelengths which are similar to the wavelengths of the second and/or third bands of electromagnetic radiation.

34. An apparatus for sorting as claimed in claim 32, and wherein the first band of electromagnetic radiation has wavelengths which are dissimilar from the wavelengths of the second and/or third bands of electromagnetic radiation.

35. An apparatus for sorting as claimed in claim 32, and wherein the line scan imaging assembly includes multiple line scan imaging assemblies, and wherein each of the line scan imaging assemblies are oriented so as to view an outwardly facing surface of the electromagnetic radiation diffuser element.

36. An apparatus for sorting as claimed in claim 32, and wherein the laser scanner has a predetermined viewing orientation relative to the line of sight and background element, respectively, and wherein the line scan imaging assembly has a viewing orientation which is the same as the laser scanner.

37. An apparatus for sorting as claimed in claim 32, and wherein the laser scanner has a predetermined viewing orientation relative to the line of sight, and the background element, respectively, and wherein the line scan imaging assembly has a viewing orientation which is different from that of the laser scanner.

38. An apparatus for sorting as claimed in claim 32, and wherein the selectively energizable radiator has a predetermined spatial orientation relative to the inspection station, and which further facilitates the illumination of the line of sight with the third band of electromagnetic radiation, and simultaneously avoids an illumination of the background element with the third band of electromagnetic radiation.

39. An apparatus for sorting as claimed in claim 32, and wherein the controller, in a first mode of operation, selectively energizes the electromagnetic radiation emitters which are enclosed within the background element, and simultaneously, and selectively adjusts the radiance of the respective, energized, electromagnetic radiation emitters so as to provide a resulting, and predetermined, background illumination which can be detected by each of the line scan imaging assembly, and the first electromagnetic radiation detector which is operably coupled with the laser scanner.

40. An apparatus for sorting as claimed in claim 39, and wherein the controller, in the first mode of operation, and upon receiving the electrical signal generated by the line scan imaging assembly, and which identifies the predetermined background illumination emitted by the background, interprets the received electrical signal as a view of the background, and wherein other, different electrical signals received from the line scan imaging assembly are interpreted by the controller as being products, or objects of interest which are positioned in a given location along the line of sight.

41. An apparatus for sorting as claimed in claim 39, and wherein the controller, in the first mode of operation, and upon receiving an electrical signal from the first electromagnetic radiation detector, and which is operably coupled with the laser scanner, interprets the received electrical signal as a view of the predetermined, background illumination emitted by the background, and wherein other, different, electrical signals received from the first electromagnetic radiation sensor are interpreted by the controller as being products, or objects of interest which are located along the line of sight of the laser scanner, and at a location which is indicated by a position of the laser flying spot along the line of sight.

42. An apparatus for sorting as claimed in claim 41, and wherein the apparatus includes a first, modified, electromagnetic radiation detector which has been rendered operable to detect the wavelengths of the first band of the electromagnetic radiation which is emitted by the background element, but which is transmitted by the electromagnetic radiation diffuser element, and then forms a corresponding electrical signal, and wherein the controller, in the first mode of operation, and upon receiving the electrical signal from the first, modified electromagnetic radiation detector, interprets the electrical signal as a view of the background element, and wherein other, different electrical signals, are interpreted by the controller as being products or objects of interest which are located along the line of sight of the laser scanner, and at a location which is indicated by a position of the laser flying spot along the line of sight.

43. An apparatus for sorting as claimed in claim 42, and wherein the controller, in the first mode of operation, receives and processes both the electrical signals from first modified electromagnetic radiation detector, and the second electromagnetic radiation detector so as to increase a contrast of an image formed by the controller of the line of sight, and improve the detection of the products, and the objects of interest passing through the inspection station.

44. An apparatus for sorting as claimed in claim 32, and wherein the controller, in a second mode of operation, selectively deenergizes the electromagnetic radiation emitters of the background element, and thereby causes the background element to appear dark because of the absence of any emitted background illumination, and wherein the electromagnetic radiation diffuser is operable to interact with the laser flying spot beam formed from the second band of electromagnetic radiation so as to diffuse, and scatter, the second band of electromagnetic radiation, and wherein the electrical signal produced by the line scan imaging assembly has a given electrical signal level which is interpreted by the controller as the background element, and wherein electrical signals which are received by the controller, and which are further different from the given electrical signal level generated by the background element, are subsequently interpreted by the controller as products or objects of interest positioned along the line of sight.

45. An apparatus for sorting as claimed in claim 32, and wherein the second electromagnetic radiation detector receives the scattered, second band of electromagnetic radiation from the background element diffuser, and the controller interprets the scattered, second band of electromagnetic radiation detected by the second electromagnetic radiation detector as the background element.

46. An apparatus for sorting as claimed in claim 45, and wherein the apparatus further includes a first, modified electromagnetic radiation detector which has been rendered operable to sense the first band of electromagnetic radiation which has been emitted by the background element, and then forms a corresponding electrical signal which has a given electrical signal level, and wherein the controller interprets the sensing of the first source of electromagnetic radiation by the first, modified electromagnetic radiation detector at the given electrical signal level as the background, and wherein the controller interprets other, different electrical signal levels as indicating the presence of products, or objects of interest within the field of view, and at a location which is correlated with the position of the laser flying spot beam along the line of sight.

47. An apparatus for sorting as claimed in claim 32, and wherein the controller selectively energizes the multiplicity of selectively energizable electromagnetic radiation emitters to emit given wavelengths of electromagnetic radiation which may not be detected by either the first or second electromagnetic radiation detectors, or which may be detected by one, or the other of the first or second electromagnetic radiation detectors.

48. An apparatus for sorting as claimed in claim 47, and wherein the controller selectively energizes the multiplicity of selectively energizable electromagnetic radiation emitters so as to emit predetermined, discreet, wavelength bands of electromagnetic radiation which are sensed as one, predetermined, discreet, wavelength band by the line scan imaging assembly, and a second, discreet, wavelength band by the laser scanner.

49. An apparatus as claimed in claim 48, and wherein the respective products and objects of interest each have a predetermined spectral and/or scatter response characteristic, and wherein the controller selectively energizes at least some of the electromagnetic radiation emitters which are enclosed within the background element so that the emitted electromagnetic radiation of the background element provides an increased contrast relative to the products or objects of interest passing through the inspection station, and which increases the ability of the laser scanner, line scan imaging assembly, and the controller to detect the product, and the objects of interest in the product stream passing through the inspection station.

* * * * *

UNITED STATES PATENT AND TRADEMARK OFFICE
CERTIFICATE OF CORRECTION

PATENT NO. : 10,486,199 B2
APPLICATION NO. : 15/868027
DATED : November 26, 2019
INVENTOR(S) : Timothy L. Justice et al.

It is certified that error appears in the above-identified patent and that said Letters Patent is hereby corrected as shown below:

In the Specification

Column 3: Line 30: Insert the letter --s-- after element.

Column 4: Line 12: Insert the letter --s-- after element.

Column 5: Line 34: Insert the letter --s-- after element.

Column 5: Line 41: Insert the letter --s-- after element.

Column 7: Line 50: Delete the letter --s-- from shows. (2nd occurrence of "s")

Column 13: Line 6: Delete the word "can" and insert the word --scan--.

Column 19: Line 71: Insert a --.-- after (FIGS.1,2,3, and 7).

In the Claims

Column 24: Line 51: Claim 7 Delete the word "the".

Column 27: Line 49: Claim 23 Delete second of the phrases "along the".

Column 29: Line 14: Claim 28 Insert the letter --s-- after element.

Column 29: Line 18: Claim 28 Insert the letter --s-- after element.

Column 30: Line 2: Claim 29 Insert the letter --s-- after element.

Signed and Sealed this
Eleventh Day of August, 2020

Andrei Iancu
*Director of the United States Patent and Trademark Office*

Column 32: Line 60: Claim 41 Insert the word --beam-- after the word --spot--.

Column 33: Line 10: Claim 42 Insert the word --beam-- after the word --spot--.